(12) United States Patent
Yokoi

(10) Patent No.: US 6,459,484 B1
(45) Date of Patent: Oct. 1, 2002

(54) SCANNING OPTICAL APPARATUS

(75) Inventor: Eiji Yokoi, Hix Hills, NY (US)

(73) Assignee: Olympus Optical Co., Ltd., Tokyo (JP)

( * ) Notice: Subject to any disclaimer, the term of this patent is extended or adjusted under 35 U.S.C. 154(b) by 160 days.

(21) Appl. No.: 09/692,141

(22) Filed: Oct. 20, 2000

(30) Foreign Application Priority Data

Oct. 21, 1999 (JP) ............................................ 11-299373
Mar. 10, 2000 (JP) ...................................... 2000-072506

(51) Int. Cl.$^7$ ............................................. G01N 21/64
(52) U.S. Cl. ...................................................... 356/318
(58) Field of Search .......................... 356/73, 319, 320, 356/326, 300, 317, 318; 250/458.1, 459.1, 461.1, 461.2, 201.3, 234–236

(56) References Cited

U.S. PATENT DOCUMENTS 5,329,352 A * 7/1994 Jacobsen ..................... 356/301
5,751,417 A    5/1998 Uhl
6,255,646 B1 * 7/2001 Shimada ..................... 250/234
6,377,344 B2 * 4/2002 Schoeppe ................... 356/318

FOREIGN PATENT DOCUMENTS

JP    2000-199855    7/2000
WO   WO 95/07447    3/1995

* cited by examiner

Primary Examiner—Michael P. Stafira
(74) Attorney, Agent, or Firm—Pillsbury Winthrop LLP

(57) ABSTRACT

A scanning optical apparatus includes a light source unit, an objective lens, a scanning device, an imaging optical system, a confocal aperture, a plurality of photodetectors, a spectrum decomposing element, and a light-deflecting microelement array. The light source unit is located at the position where illumination light from the light source unit is incident through the light-deflecting microelement array on the confocal aperture. Each of light-deflecting microelements constituting the light-deflecting microelement array has deflection angles for selectively deflecting light passing through the confocal aperture toward the plurality of photodetectors and a deflection angle for deflecting the light from the light source unit toward the confocal aperture so that each of the light-deflecting microelements is capable of selecting one of these deflection angles.

22 Claims, 15 Drawing Sheets

SCANNING OPTICAL APPARATUS

BACKGROUND OF THE INVENTION

1. Field of the Invention

This invention relates to a scanning optical apparatus which is capable of detecting a plurality of beams of emission light (fluorescent light) simultaneously.

2. Description of Related Art

In general, fluorescence photodetectors are used in many fields including medicine and biology for the purpose of detecting protein and genes in which living tissues and cells are labeled by fluorescence. In particular, a multiple-fluorescence detection technique that a specimen stained by a plurality of fluorescent dyes is observed at a time has recently been used to exercise its power for the analysis of a gene and the clarification of an intracellular structure.

As an effective means of such fluorescence detection, a laser scanning microscope (LSM) is well known. FIG. 1 shows a typical arrangement of an optical system of the LSM for fluorescence. In this LSM, laser beams emitted from three laser oscillators is 101a, 101b, and 101c which have different oscillation wavelengths are combined on a common optical path by laser-beam combination dichroic mirrors 102a and 102b. After that, a combined laser beam is enlarged to a beam diameter of proper size through a beam expander 103 and is reflected by a dichroic mirror 104. The laser beam is then deflected by an X-Y scanning optical system 105, and after being collected through a pupil relay lens 106 and an objective lens 107, irradiates a specimen 108. The specimen 108 is thus scanned with a laser spot, and emission light from the specimen 108, excited by the irradiation of the laser beam, follows a path from the objective lens 107 to the dichroic mirror 104, and after being transmitted through the dichroic mirror 104, is separated by a dichroic mirror 109a for separation. Emission light reflected by the dichroic mirror 109a is condensed by an imaging lens 110a and passes through a confocal aperture 111a. After light with wavelengths other than that of the first emission light required is absorbed or reflected by an emission filter 112a, the intensity of the first emission light is detected by a photodetector 113a. The confocal aperture 111a is placed at a position optically conjugate with the focal point of the objective lens 107 and blocks light other than the first emission light excited by the laser spot. An image thus obtained has a very high contrast. Moreover, a distance between the specimen 108 and the objective lens 107 is relatively changed along the optical axis, and thereby a three-dimensional image can be obtained.

On the other hand, emission light transmitted through the dichroic mirror 109a is further separated by a dichroic mirror 109b. Emission light reflected by the dichroic mirror 109b is condensed by an imaging lens 110b and passes through a confocal aperture 111b. Through an emission filter 112b transmitting only the second emission light required, the intensity of the second emission light is detected by a photodetector 113b. Emission light transmitted through the dichroic mirror 109b is condensed by an imaging lens 110c and passes through a confocal aperture 111c. Through an emission filter 112c transmitting only the third emission light required, the intensity of the third emission light is detected by a photodetector 113c. The optical system mentioned above is capable of detecting simultaneously triple-excitation emission light with three wavelengths emitted from the laser oscillators 101a, 101b, and 101c. Whenever the conditions of multiple excitation, such as wavelengths of laser beams, the kind of fluorescent dye, and the number of excitation laser oscillators, are changed, the dichroic mirror 104, the dichroic mirrors 109a and 109b, and the emission filters 112a, 112b, and 112c are replaced with filters having the optimum dispersion characteristics.

However, a conventional LSM for fluorescence using these optical filters has the following problems. First, the optical filters, because of their fabrication restrictions, cannot be designed to determine dispersion characteristics at will, and thus the amount of emission light and the S/N ratio are limited. In particular, the emission filter must completely block excitation light, but a filter that sufficiently transmits light in the wavelength region of the highest fluorescence intensity, close to the wavelength of the excitation light, cannot be fabricated at present. Second, expensive optical filters which are exclusively used in accordance with the wavelength of the excitation light and the fluorescent dye must be prepared. When a variety of multiple excitation are taken into account, it is unavoidable to cause an increase in the number of filters and the complication and oversizing of an apparatus used. Third, in the optical system of the LSM for fluorescence, multiple fluorescence is dispersed through a plurality of optical filters, and hence an appreciable amount of light is lost before emission light reaches each of the photodetectors. Any of these problems becomes severe as the multiplicity of excitation light and emission light increases.

In order to solve the above problems, techniques of selecting and detecting a plurality of fluorescence wavelengths without using the optical filters are proposed. For example, WO 95/07447 discloses a spectroscope and a confocal fluorescence microscope in which a light beam decomposed into a wavelength spectrum by a prism is dispersed into a first wavelength region transmitted through a slit-like mirror and a second wavelength region reflected thereby, and the position and width of a second slit restricting the slit-like mirror and the second wavelength region are controlled so that two arbitrary wavelength regions can be selected and detected. On the other hand, Japanese Patent JP-A-2000-199855 discloses a scanning optical apparatus in which emission light transmitted through a confocal aperture is decomposed by a prism into a wavelength spectrum, which is received by a light-deflecting microelement array such as a digital mirror array (DMD). In this case, each of light-deflecting microelements has light-deflection angles that cause emission light to be received by a plurality of photo-detectors, and the light-deflection angles are arbitrarily selected so that the optimum fluorescence detection is always made with respect to various combinations of wavelengths of excitation light and fluorescent dyes and a multiple fluorescence image with a high S/N ratio can be obtained. In these techniques, however, filters for the separation of emission light are merely dispensed with, and a dichroic mirror for excitation cannot be removed.

U.S. Pat. No. 5,751,417, by contrast, discloses a confocal LSM which dispenses with the dichroic mirror for excitation. In this LSM, incident excitation light is transmitted through a slit array and is separated in wavelength by a first spectroscope. Separated excitation light is projected at the position where the light is reflected by a wavelength selective member which is a slit array transmitted through emission light and reflecting excitation light. Reflected excitation light is projected on a confocal slit array by a second spectroscope which is identical with the first spectroscope, and irradiates a specimen through an imaging lens, a scan mirror, and an objective lens. Emission light produced by the irradiation of the excitation light follows a reverse course, and after being transmitted through the confocal slit array and separated in wavelength by the second spectroscope, is projected on the wavelength selective member. Here, since the wavelength of emission light is transmitted and the wavelength of excitation light is reflected, the excitation light reflected by the specimen and the emission light are separated. The emission light transmitted through the wavelength selective member is spatially returned to an original wavelength spread by a third spectroscope which is identical with the first and second spectroscopes, and after being transmitted through the slit array disposed at a position conjugate with the confocal slit array, is imaged by an area sensor or a multiline sensor. By changing the slit width and position of the wavelength selective member, the wavelength regions of excitation light and emission light obtained can be changed. It is also described that pinholes are used instead of slits, and the DMD is used as the wavelength selective member.

The technique disclosed in U.S. Pat. No. 5,751,417 involves the use of a means for changing the wavelength region of emission light as excitation light due to single-wavelength excitation, that is, specifically, a means for moving a slit- or pinhole-like wavelength selective stop in the direction of the separation of wavelength or changing the size of the stop. However, this technique does not in any way suggest a means of detecting a plurality of fluorescence wavelengths simultaneously and a means for accommodating the variety of excitation wavelengths and fluorescent dyes, and fails originally to provide a method effective for a fluorescence detecting means of multiple excitation. Although this publication also discloses that the wavelength selective stop is replaced by the DMD, it is difficult to understand additional functions and effects in this case. Furthermore, a laser is not assumed as a light source, and thus when account is taken of the influence of return light on the laser, necessarily caused in constructing an apparatus, the use of the laser may be difficult.

Apart from this, an LSM provided with an apodization filter at the position of the pupil of an objective lens or at a conjugate position thereof is well known. Here, apodization refers to a technique used for the purpose of improving resolution and emphasizing a moderate or low contrast by imparting an amplitude distribution or a phase distribution to a light beam passing through the pupil to change the profile of a point spread function. This technique is widely applied, not to speak of the LSM.

When only a desired wavelength of emission light is selected from a light beam whose wavelength is spatially decomposed, it is necessary to consider a spatial energy distribution of excitation light reaching a wavelength selective means. It is for reason that since the emission efficiency of fluorescence caused by the irradiation of excitation light is very low, the excitation light reflected and scattered by a specimen is much stronger than the emission light, and if the excitation light, although slight, is mixed with the emission light, it becomes a background noise to considerably degrade the S/N ratio of an image.

In this respect, the technique set forth in each of WO 95/07447 and Hei 11-072544 fails to fully discuss a spatial spread of excitation light in the process that the excitation light is removed and only emission light is separated and detected. As a result, the separation between excitation light and emission light becomes incomplete and it is difficult to obtain a high S/N ratio. Alternatively, if a beam of emission light mixed with excitation light is eliminated, the amount of emission light used as a signal will be materially reduced, and it likewise becomes difficult to obtain a high S/N ratio.

On the other hand, the technique of apodization is to impart a transmittance distribution to a light beam in the pupil and thus a loss in the amount of light is necessarily caused. In particular, when the apodization is applied to a beam of emission light in an apparatus required for fluorescence detection, the amount of emission light which is originally faint is further lost and a sufficient signal cannot be obtained. This deteriorates the S/N ratio. Hence, the application of the apodization to the beam of emission light in a fluorescence photodetector brings about a big problem.

SUMMARY OF THE INVENTION

It is, therefore, a primary object of the present invention to provide a scanning optical apparatus which has a simple structure which does not use optical filters, notably a filter for fluorescence separation nor a dichroic mirror for excitation, and dispenses with a mechanical drive requiring a high degree of accuracy of positional reproducibility, and is capable of detecting a multiple fluorescent image of a multiply stained specimen with a high S/N ratio, without changing the construction of the apparatus with respect to various combinations of excitation wavelengths with fluorescent dyes.

It is another object of the present invention to provide a scanning optical apparatus with a high S/N ratio.

In order to achieve the above objects, according to one aspect of the present invention, the scanning optical apparatus includes a light source unit; an objective lens for collecting illumination light emitted from the light source unit on a specimen; a scanning means for relatively moving collected light and the specimen; an imaging optical system for imaging light emanating from the specimen; a confocal aperture placed at a position conjugate with the focal point of the objective lens; a plurality of photodetectors for detecting the light from the specimen, passing through the confocal aperture; a first spectrum decomposing element for spatially decomposing the light passing through the confocal aperture into a spectrum; and a light-deflecting microelement array comprised of a plurality of light-deflecting microelements, receiving light from the first spectrum decomposing element through a first collecting optical system to deflect the light toward the photodetectors. In this case, the light source unit is located at the position where the illumination light is incident through the light-deflecting microelement array on the confocal aperture. Each of the light-deflecting microelements has deflection angles for selectively deflecting the light passing through the confocal aperture toward the plurality of photodetectors and an deflection angle for deflecting the light from the light source unit toward the confocal aperture so that each of the light-deflecting microelements is capable of selecting one of these deflection angles. By doing so, excitation light causing a reduction in contrast is completely eliminated, a plurality of fluorescent beams can be easily separated simultaneously, the optimum fluorescence detection always becomes possible, and a bright image with a high S/N ratio is obtained with respect to multiple emission light.

According to another aspect of the present invention, the scanning optical apparatus includes a light source unit; an objective lens for collecting a light beam emitted from the light source unit on a specimen; a scanning means for relatively scanning the specimen with a collected spot; an imaging optical system for imaging light emanating from the specimen; a confocal aperture placed at a position conjugate with the focal point of the objective lens; a plurality of photodetectors for detecting the light from the specimen, passing through the confocal aperture; a dispersion element for spatially decomposing a light beam passing through the confocal aperture into a spectrum; and a wavelength selective means for receiving a part of the light beam decomposed into a spectrum to deflect it toward any of the plurality of photodetectors. In this case, an apodization filter is interposed between the confocal aperture and the dispersion element.

According to still another aspect of the present invention, the scanning optical apparatus includes a light source unit; an objective lens for collecting a light beam emitted from the light source unit on a specimen; a scanning means for relatively scanning the specimen with a collected spot; an imaging optical system for imaging light emanating from the specimen; a confocal aperture placed at a position conjugate with the focal point of the objective lens; a plurality of photodetectors for detecting the light from the specimen, passing through the confocal aperture; a dispersion element for spatially decomposing a light beam passing through the confocal aperture into a spectrum; and a light-deflecting microelement array arranged, at least, in the direction of spectral decomposition and receiving a part of the light beam decomposed into a spectrum to deflect it toward any of the plurality of photodetectors. Each of light-deflecting microelements has a plurality of deflection angles that cause light beams to be selectively received by the plurality of photodetectors, and an apodization filter is interposed between the confocal aperture and the dispersion element.

These and other objects as well as the features and advantages of the present invention will become apparent from the following detailed description of the preferred embodiments when taken in conjunction with the accompanying drawings.

DETAILED DESCRIPTION OF THE PREFERRED EMBODIMENTS

Figure 1:
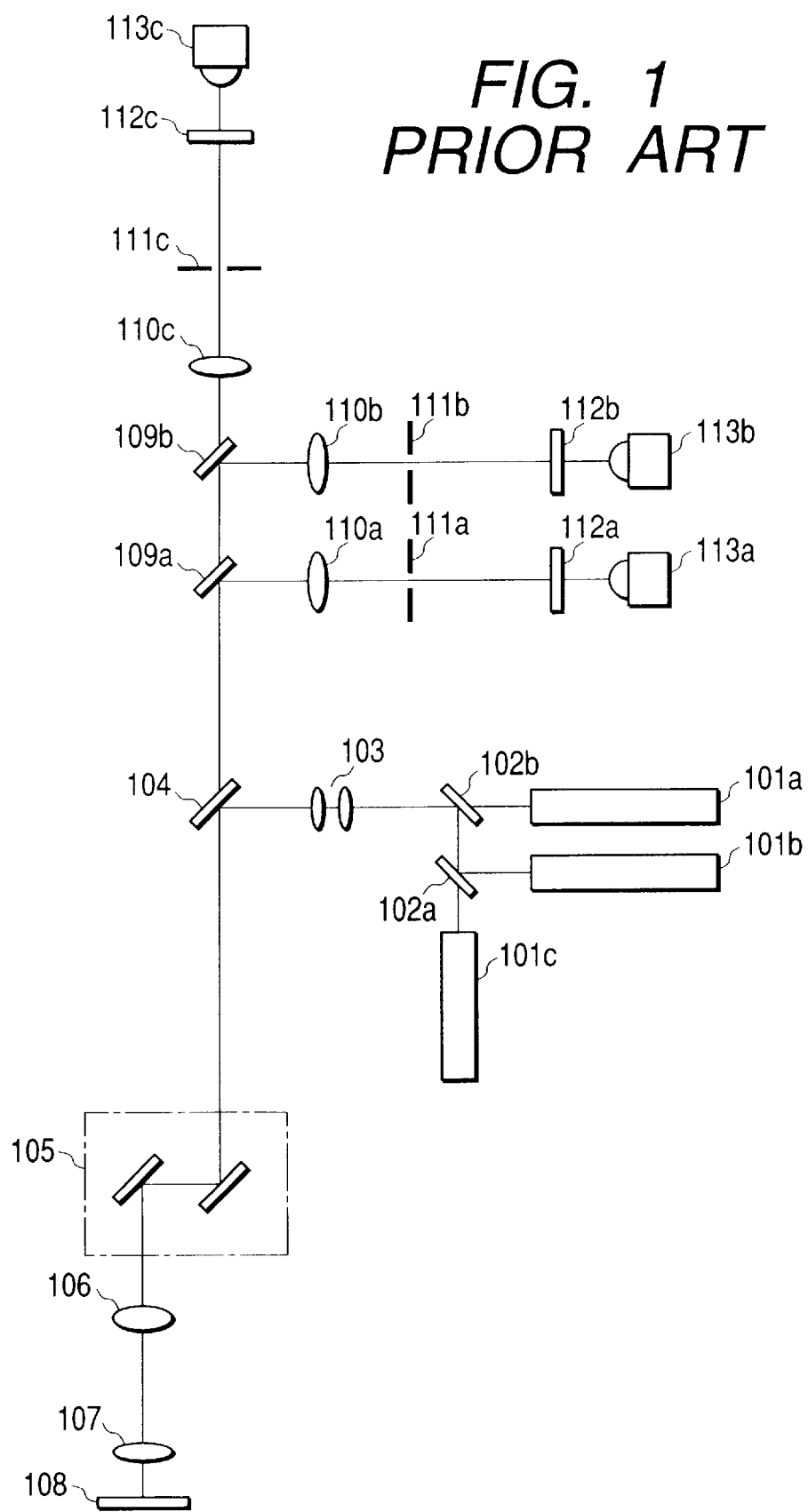
FIG. 1 is a view showing an optical arrangement of a conventional laser scanning microscope for fluorescence.

The scanning optical apparatus of a first aspect will be first described below. This scanning optical apparatus, as mentioned above, is capable of observing a multiple fluorescent image of a multiply stained specimen with a small number of optical filters and without a mechanical drive, and also has the following features.

The scanning optical apparatus of the present invention has a second spectrum decomposing element equal in the amount of spectrum separation to the first spectrum decomposing element and a second collecting optical system for collecting light from the second spectrum decomposing element on the light-deflecting microelement array between the light source unit and the light-deflecting microelement array. Consequently, even when a light source unit emitting light with a plurality of wavelengths is used, optical alignment can be achieved with ease and accuracy and it becomes possible to downsize the apparatus.

The scanning optical apparatus of the present invention is provided with single-mode fibers between the light source unit and the second spectrum decomposing element. Consequently, a change or switch of light from the light source unit is facilitated. Moreover, it becomes easy to project the light from the light source unit with accuracy at a predetermined position on each light-deflecting microelement, and an image with a high S/N ratio can be obtained.

The scanning optical apparatus of the present invention is also provide with a coupling optical system which renders light with a plurality of wavelengths incident on each of the single-mode fibers. By doing so, even when a laser is used as a light source, it is avoidable that the stability of laser oscillation is impaired by reflected light from the specimen, and fluorescent image with a high S/N ratio can be obtained. The single-mode fiber has a very small core diameter and its exit end may be thought of as a nearly ideal point source. Thus, it has the advantages that high wavelength resolution can be ensured and the optical axis of a laser beam emerging from the exit end is adjusted independently, irrespective of the location of the laser, to thereby facilitate a change or switch of the laser. Furthermore, since the exit points and optical axes of a plurality of laser beams can be made to coincide completely, it becomes easy to project individual laser beams with accuracy at preset positions on the light-deflecting microelements.

The scanning optical apparatus of the present invention has an optical isolator between the light source unit and the second spectrum decomposing element. Consequently, when the laser is used as a light source, a laser beam scattered by the specimen is prevented from returning to the laser, and a stable laser output can be obtained.

The scanning optical apparatus of the present invention is designed to satisfy a condition: 0.2<NA1/NA2<3, where NA1 is the numerical aperture of light passing through the confocal aperture, incident on the light-deflecting microelement array and NA2 is the numerical aperture of light incident from the light source unit on the light-deflecting microelement array. If the value of NA1/NA2 exceeds the upper limit of 3, the diameter of a spot formed on the light-deflecting microelement array by an incident laser beam becomes extremely larger than that of a spot formed on the light-deflecting microelement array by emission light emanating from the specimen, and thus wavelength resolution where excitation light and emission light are separated is deteriorated. As a result, the wavelength region of emission light to be detected is narrowed, and in view of brightness and the S/N ratio, the performance of the apparatus cannot be completely exercised. Below the lower limit of 0.2, the utilization efficiency of the laser beam as the excitation light is appreciably impaired and a costly, great power laser must be used to obtain a sufficient amount of light. Also, a sufficient amount of light for the excitation light may not be obtained, depending on the laser wavelength used. Furthermore, if the numerical aperture NA2 is much higher than is necessary, it becomes difficult to correct the aberration of the collecting optical system, and a large-diameter lens system using a large number of lenses is required to thereby cause the complication and oversizing of the apparatus.

The scanning optical apparatus of the present invention is such that the second spectrum decomposing element is located at a position optically conjugate with the first spectrum decomposing element. Whereby, a light beam separated at an angle by the second spectrum decomposing element is restored in separation at an angle by the first spectrum decomposing element located at its conjugate position. Therefore, a laser beam with any wavelength is capable of passing through the confocal aperture along the same optical axis, and defects in misalignment can be obviated.

The scanning optical apparatus of the present invention is provided with a control device including a memory section for storing individual deflection angles of the light-deflecting microelements, an information input section for inputting the information of wavelengths of the light source unit and fluorescent dyes, and a control section for reproducing the individual deflection angles of the light-deflecting microelements stored from the information inputted by the information input section. Whereby, lasers and fluorescent dyes which are often used and a state of an apparatus corresponding to fluorescence detection made once can be reproduced at any time by a simple input to the information input section. Thus, elaborate work on measurement is lightened and a comfortable operation is ensured. Moreover, measurement errors are eliminated, and the damage and bleaching of the specimen caused by the irradiation of a strong laser beam can be kept to a minimum.

The scanning optical apparatus of the present invention is also designed to detect the positions of the light-deflecting microelements corresponding to the wavelengths of the light source unit and to determine the individual deflection angles of the light-deflecting microelements, on the basis of detected positional information. A laser beam for excitation is transmitted through the confocal aperture by some means, for example, in such a way that it is reflected by a mirror located at the position of the specimen, and is introduced through the second spectrum decomposing element to the light-deflecting microelement array. In this case, each of the light-deflecting microelements is directed toward each of the photodetectors to detect the amount of light of the laser beam, and thereby the position of each light-deflecting microelement corresponding to the wavelength of the laser beam for excitation can be detected. In accordance with this information, the deflection angle of each light-deflecting microelement is determined, and thereby the calibration of the apparatus relative to changes by time and ambience of the laser wavelength is performed, so that multiple emission light can be always detected with the highest S/N ratio. A fully automatic system can be constructed in association with the oscillation mechanism of the laser.

The scanning optical apparatus of the present invention also includes photodetectors for detecting emission light emanating from the specimen and photodetectors for detecting light reflected by the specimen. Light beams incident on the light-deflecting microelement array may be scattered in directions other than desired directions by gaps between the microelements or surface flaws or edges of the microelements. In particular, when such scattered light is caused by excitation light returning from the specimen, scattered excitation light is mixed with emission light to be obtained and an image contrast is materially degraded by the noise of the excitation light. Thus, in the present invention, only the excitation light, of light beams incident on the light-deflecting microelement array, is monitored by at least one photodetector so that a background noise attributable to the excitation light is estimated and only a background noise component can be correctly subtracted from intensity information obtained by other photodetectors. As a result, an image with a very high S/N ratio can be obtained. This technique has the feature that it is not virtually affected by the time fluctuation of the noise component because the background noise and the emission light are detected at exactly the same time.

The scanning optical apparatus of the present invention is such that the light-deflecting microelements are mirror microelements. Consequently, the step widths of a plurality of deflection angles are made relatively large and thus a separation between emission light and excitation light can be securely performed. Moreover, a drive for mirrors can be located on the backside of reflecting surfaces and the utilization efficiency of light can be much improved.

Subsequently, the scanning optical apparatus of each of second and third aspects will be described below. This scanning optical apparatus is capable of obtaining a higher S/N ratio. What follows is a description of its function.

Figure 2:
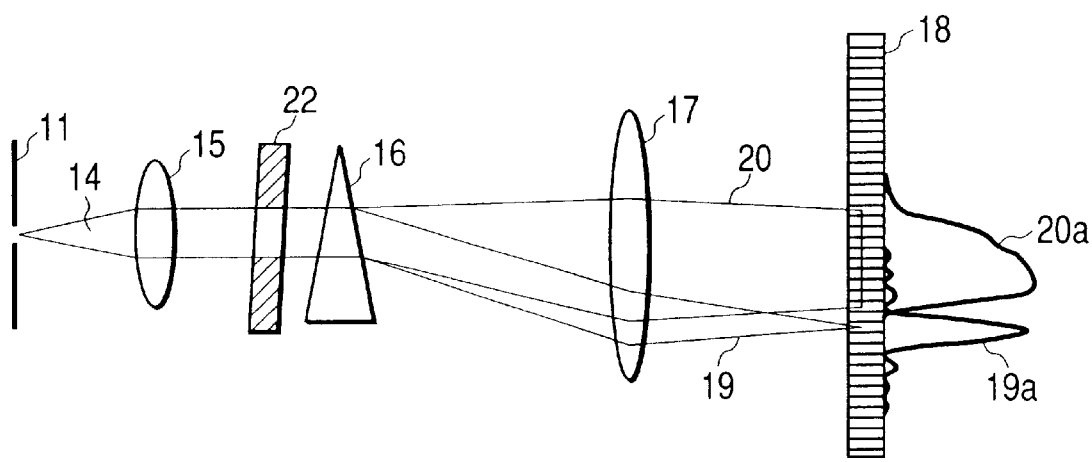
FIG. 2 is a view for explaining the principle of a wavelength separation in the scanning optical apparatus according to the present invention.
Figure 3:
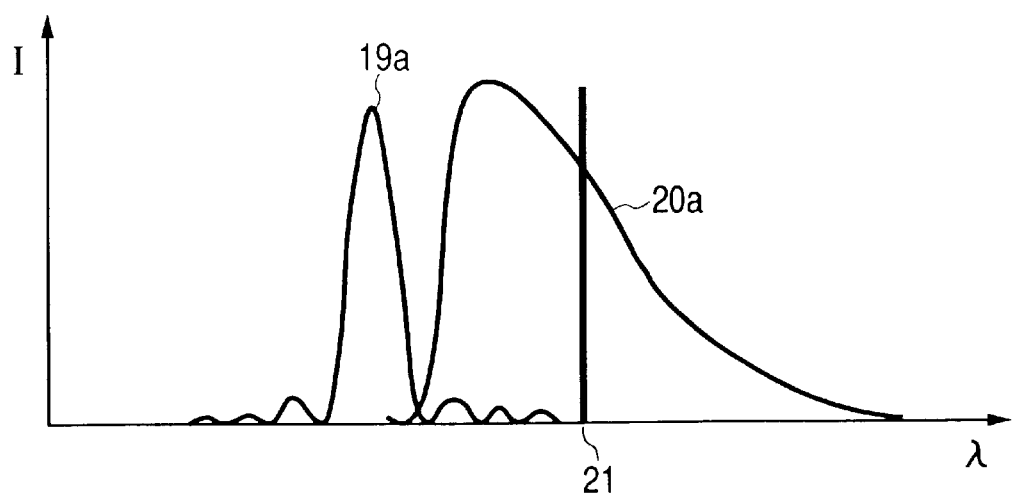
FIG. 3 is a graph showing intensity distributions of an excited beam and a fluorescent beam on a wavelength selective means in the present invention.

FIG. 2 shows the principle of the wavelength separation in the scanning optical apparatus of the present invention. First of all, reference is made to the case where an optical element 22 is not placed in the optical path. In the scanning optical apparatus of FIG. 2, a light beam 14 passing through a confocal aperture 11 is rendered nearly parallel by a collimating lens 15 and is collected, through a dispersion element 16 and a collector lens 17, on a wavelength selective means 18 in accordance with a spectrum. In FIG. 3, the intensity distributions of an excited beam 19 and a fluorescent beam 20 on the wavelength selective means 18 in this case are represented by reference numerals 19a and 20a, respectively. In this figure, the abscissas are wavelengths converted into positional information by the dispersion element 16 and the ordinates are the intensities of light beams reaching the wavelength selective means 18. Here, the excited beam 19 has a very narrow wavelength region (monochrome in a laser), and therefore, as in the distribution 19a, assumes a narrow intensity distribution, namely a so-called airy pattern. On the other hand, the fluorescent beam (emission light) 20, which has a wide wavelength region, is thought of as a superposition of airy patterns with different intensities, formed in accordance with wavelengths, and assumes a wide intensity distribution as in the distribution 20a.

The wavelength selective means 18 is designed to eliminate excitation light from a light beam reaching thereto and to make a wavelength selection of wavelengths so that only emission light can be detected. In this case, it is important to determine a separation wavelength 21 which is a wavelength forming the boundary between the emission light to be detected and the excitation light to be eliminated. This is because the ratio between the amount of emission light used as the signal of an image of the emission light to be detected and the amount of excitation light responsible for a noise, namely the S/N ratio, is determined by the value of the separation wavelength 21. In order to detect (capture) a great deal of emission light, it is desirable that the separation wavelength 21 is set as close to the excitation wavelength as possible.

In the past, however, it has been impossible to make the separation wavelength 21 close to the excitation wavelength, and a great deal of emission light has not been captured. This is because a spot formed on the wavelength selective means 18 with respect to each wavelength is not a point, but has a spatial energy distribution, and the fluorescence wavelength and the excitation wavelength, each having a spread, overlap each other in some wavelength region.

For example, when the light beam 14 has a uniform amplitude distribution, the intensity distribution 19a on the wavelength selective means 18, as shown in FIG. 3, is such that a distance to a position where the intensity of light first becomes zero is short. The intensity distribution 19a, however, is attenuated while repeating the ascent and descent of a curve and a zero intensity (this portion is called a side lobe). Hence, the excitation light 19 has the intensity distribution of light (energy distribution) over a very wide wavelength region form the center of the spot. In order to completely separate the excitation light 19 from the light beam 14 reaching the wavelength selective means 18, the separation wavelength 21 must be set at a considerable distance from the center of the intensity distribution of the excitation light. Otherwise, the excitation light becomes a background noise and an image contrast will be degraded. However, if the separation wavelength 21 is set in this way, a great deal of emission light will be eliminated, together with the excitation light, and therefore it is difficult to obtain an image with a good S/N ratio.

Thus, the optical element 22 which is an apodization filter is interposed between the confocal aperture 11 and the dispersion element 16, and amplitude modulation is applied to the light beam 14 to change the intensity distribution 19a of the spot of the excitation light so that the intensity distribution of the excitation light 19 is prevented from spreading over a wide wavelength region. By doing so, the separation wavelength 21 set by the wavelength selective means can be made to approach the excitation wavelength as far as possible. Consequently, the amount of emission light to be detected is increased and the S/N ratio can be rapidly improved.

Figure 4A:
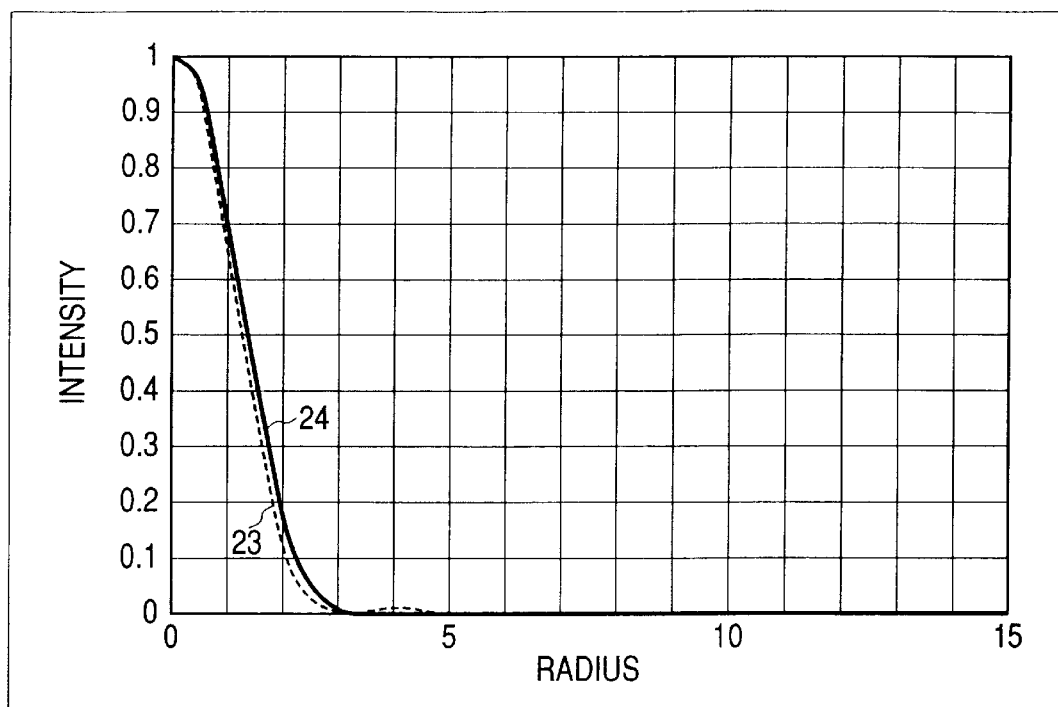
FIG. 4A is a graph showing the profiles of spots relative to the apodization of a light beam with a uniform amplitude distribution.

FIG. 4A shows the profiles of spots where apodization with a Gaussian amplitude distribution truncated so as to have an amplitude of 1/e with the largest outside diameter of a light beam is applied to the light beam 14 with a uniform amplitude distribution and where it is not applied thereto, using FIG. 2. In FIG. 4A, the abscissas are distances (radii) from the center of the spot and the ordinates are relative intensities where an intensity at the center of the spot is taken as 1. Reference numeral 23 represents the intensity distribution of light where the apodization is not applied and 24 represents the intensity distribution of light where the apodization is applied. Also, a calculation in this graph is performed as a wavelength=488 nm and an NA=0.1.

As seen from FIG. 4A, the intensity distribution 24 where the apodization is applied is such that a radius where the intensity of light first becomes zero is larger than that of the intensity distribution 23 where the apodization is not applied (In FIG. 4A, the radius where the intensity of light first becomes zero is somewhat smaller than 3 for the intensity distribution 23 and is somewhat larger than 3 for the intensity distribution 24). However, the intensity distribution 23 show the ascent and descent of a curve after the intensity of light has become zero, whereas the intensity distribution 24 remains zero thereafter.

Figure 4B:
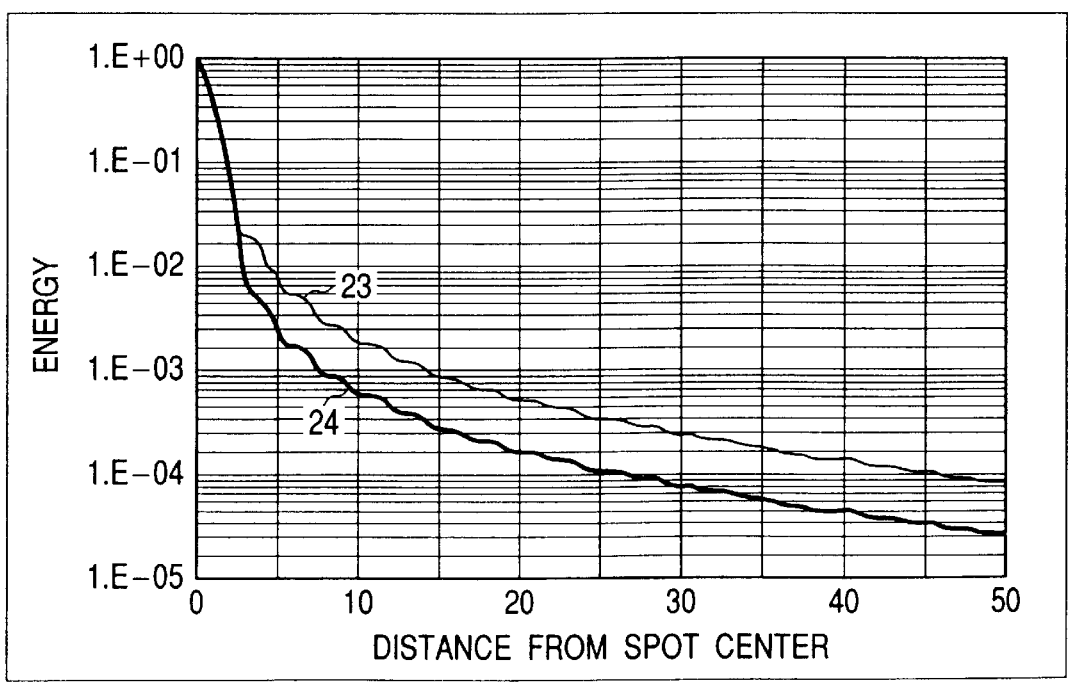
FIG. 4B is a graph showing a comparison between the amounts of excitation light at the position a separated wavelength relative to the apodization in FIG. 2.

FIG. 4B shows the result of the calculation of the amounts of excitation light contained in emission light and a comparison between them, at the position of the separation wavelength where the apodization is applied and where it is not applied, in FIG. 2. In FIG. 4B, the abscissas are distances from the center of the spot and the ordinates are relative amounts of light where the total amount of exited light reaching the wavelength selective means is taken as 1. Again, reference numeral 23 represents the profile of the amount of excitation light where the apodization is not applied and 24 represents the profile of the amount of excitation light where the apodization is applied.

FIGS. 4A and 4B, it is seen that the side lobe of the excitation light is suppressed by applying the apodization and consequently, the separation wavelength 21 can be made close to the excitation wavelength so that it becomes possible to detect emission light more copiously.

When the apodization is applied, a light beam traveling through the apodization filter 22 is lost in the amount of transmitted light by the amplitude distribution of the apodization filter 22. However, the amount of emission light which can be detected by the wavelength selective means, in contrast with the amount of light lost by the apodization filter 22, is materially increased and as a result, the signal of the a fluorescent image is increased. That is, with a single technique of the apodization, the amount of emission light, because of its transmittance, is merely lost. However, as in the present invention, when fluorescence photodetectors using a dispersion system are combined with the apodization filter, the amount of emission light is finally increased and the S/N ratio can be rapidly improved.

The separation wavelength relative to the emission light and the excitation light, determined by the wavelength selective means, requires that it can be easily adjusted to a wavelength that the S/N ratio governed by the amount of excitation light corresponding to a noise and by the amount of emission light to a signal is maximized. This is because the fluorescence wavelength and its emission efficiency vary with the conditions of the fluorescent dye and the specimen. To correctly reproduce the separation wavelength relative to the emission light and the excitation light, optimized so that the S/N ratio is improved through the apodization filter and to obtain a fluorescent image, its reproducibility on a device making a wavelength selection is significant.

Thus, the scanning optical apparatus, as in the first aspect, is constructed so that the light-deflecting microelement array, as the wavelength selective means, is arranged in the direction of spectral decomposition, and light beams spatially separated in wavelength on the light-deflecting microelement array are deflected at angles that light-deflecting microelements corresponding to a plurality of fluorescence wavelengths cause emission light to be received by different photodetectors, and at the same time, are deflected at different angles, with which no light reaches the photodetectors detecting the emission light, by light-deflecting microelements corresponding to excitation wavelengths. Consequently, the excitation wavelengths are completely eliminated and multiple emission light is separated so that both can be detected at the same time.

According to this construction, the light-deflecting microelement array is such that since wavelength information corresponds to each of the light-deflecting microelements, as one unit, a wavelength selection is digitally exercised and its reproducibility is very high. According the present invention, a high-precision operating section or control device is not required at all, and the separation wavelength can be easily changed only by controlling a digital signal applied to the microelement array.

If the light beam passing through the confocal aperture is spread, a serious error will be caused when the light beam is decomposed into a spectrum, with a ray angle as a function of wavelength. Thus, the collimating lens for rendering the light beam passing through the confocal aperture nearly parallel and the collector lens for projecting the light beam decomposed into a spectrum by the dispersion element on the light-deflecting microelement array are provided, together with the apodization filter for suppressing the side lobe of the spot of each wavelength formed by the collector lens, at least, with respect to the direction of spectral decomposition. It is necessary that an incident beam on a spectrum decomposing means is held as parallel as possible by the collimating lens.

The light beam rendered nearly parallel is decomposed through the dispersion element into a spectrum, with a ray angle as a function of wavelength. By the placement of the collector lens for collecting the light beam decomposed into a spectrum on the light-deflecting microelement array, a location on the micromirror array can be made to correspond to a wavelength which is a function of the ray angle, with a one-to-one correspondence. That is, a collected spot can be formed at a different location in accordance with each wavelength.

Here, the spread of the excitation light on the wavelength selective means affects the S/N ratio only in the direction of spectral decomposition, and thus it is necessary that the apodization filter is designed to have the characteristic of suppressing the side lope of the spot of each wavelength, notably of the excitation light, at least, with respect to the direction of spectral decomposition. Whereby, the wavelength region of emission light to be detected can be extended toward the excitation wavelength, and a high S/N ratio can be achieved.

For a means of scanning a specimen with a laser spot, a technique of changing the angle of incidence of a light beam on an objective lens through a light-deflecting element is generally used. In this case, unless the center of swing of the light-deflecting element is conjugate with the pupil position of the objective lens, an off-axis beam returning from the objective lens will deviate from the center of swing and will be reflected in the light-deflecting element. Hence, a subsequent light beam ceases to coincide with an on-axis beam, that is, the axis of the light beam is moved in association with a scan. However, it is difficult to steadily apply proper apodization to such a moving beam.

It is thus desirable that the scanning means includes at least one light-deflecting element located at a position conjugate with the pupil position of the objective lens, and the scanning direction with the light-deflecting element is made equal to the direction of spectral decomposition.

An arrangement is made so that a scanning light-deflecting element for changing an angle in the direction of spectral decomposition is made to coincide with the pupil position of the objective lens, and the light beam is not moved in the direction of spectral decomposition in which the apodization has an effect on the improvement of the S/N ratio. By doing so, the optimum apodization effect is always achieved in the entire scanning range with respect to a light beam after passing through the confocal aperture, and an image with a high S/N ratio can be provided.

When the scan is performed in a plane perpendicular to the optical axis of the specimen, at least two scanning means become necessary. When a fluorescent image is obtained, it is desirable that, in view of a scanning speed and a loss in the amount of light, high-speed, deflectable scanning mirrors are used as the scanning means. If two scanning mirrors are placed close to a position conjugate with the pupil position of the objective lens, a pupil relay optical system interposed between the scanning mirrors is eliminated and the loss of the amount of light can be reduced.

Thus, it is desirable that the scanning means are constructed with two adjacent scanning mirrors, one of which is located at a position conjugate with the pupil position of the objective lens.

Even when the two scanning mirrors cannot be placed close to a position conjugate with the pupil position of the objective lens, one of the mirrors is located at a position conjugate with the pupil position of the objective lens. By doing so, the light beam is not moved in the direction of spectral decomposition in which the apodization has an effect on the improvement of the S/N ratio, and an image with a high S/N ratio in the entire scanning range can be provided.

It is also desirable that an apodization region is made to fluctuate in a plane perpendicular to the optical axis in association with the scanning means.

Even when the light beam passing through the confocal aperture is moved by the scan, the relative positions of the apodization filter and the light beam in the plane perpendicular to the optical axis can be kept to be constant, at least, in the direction of spectral decomposition. Therefore, even though various objective lenses with different pupil positions are used, it becomes possible to provide an image that always has a high S/N ratio in the scanning range.

It is favorable that the apodization filter is constructed with a spatial optical modulator in which amplitude modulation is possible.

If a spatial optical modulator, such as a liquid crystal, is used as the apodization filter, filtering can be changed with ease and high speed in response to the movement of the light beam involved in the scan. Also, even when a beam diameter is changed by the replacement of the objective lens, it is possible to easily accommodate the filtering suitable for this case.

The apodization filter is constructed so that the amplitude of a light beam is modulated only in the direction of spectral decomposition.

The energy distribution of the spot on the wavelength selective means has an influence on the S/N ratio where emission light is detected, only in the direction of spectral decomposition. Thus, the apodization effect is brought about only in the direction of spectral decomposition, and a detectable fluorescence wavelength region is extended toward the excitation wavelength to obtain a great deal of emission light. In addition, a loss in the amount of emission light caused by the apodization filter is reduced, and thereby the S/N ratio can be further improved.

The displacement of the optical axis, involved in a change of the beam diameter and the scan, of the light beam passing through the confocal aperture varies with the kind of objective lens. It is very cumbersome that whenever the objective lens is replaced, the apodization filter is set to a state suitable therefor.

Thus, it is favorable to provide an input section for inputting the information of objective lenses, a memory section for storing the amplitude profile of the apodization filter and the displacement of the optical axis involved in the scan, and a control section for controlling a change of the apodization region in association with the scanning means, on the basis of this input information.

The characteristics and amplitude profiles of the apodization filter suitable for objective lenses and the displacement of the optical axis involved in the scan can be easily reproduced by a simple input to the input section. Hence, elaborate work on measurement is lightened and a comfortable operation is ensured. Moreover, measurement errors are eliminated, and the damage and bleaching of the specimen caused by the irradiation of a strong laser beam can be kept to a minimum.

It is also favorable to provide an axial-displacement detecting means for detecting the displacement of the optical axis involved in the scan, between the scanning means and the dispersion element, so that the apodization region is changed in association with the scanning means, on the basis of information secured by the detecting means.

The axial-displacement detecting means is constructed so that, for example, the light beam passing through the confocal aperture is split by a dichroic mirror or a half mirror and a change of the position of a split beam is detected by a solid-state image sensor. In this case, it is desirable that the element for splitting the light beam is removably placed and is out of the optical path when emission light is detected.

In accordance with the information of the axial-displacement detecting means, adequate apodization is applied to the light beam, and thereby the apparatus is calibrated with respect to variations in pupil positions of objective lenses and a change in ambience, so that emission light can be always detected with the highest S/N ratio. Also, if the axial-displacement detecting means is associated with a position of the objective lenses on nosepiece, a fully automatic system can be constructed.

It is favorable that the scanning optical apparatus has a laser light source unit; an objective lens for collecting a light beam emitted from the laser light source unit on a specimen; a scanning means for relatively scanning the specimen with a collected laser spot; an imaging optical system for imaging light emanating from the specimen; a confocal aperture placed at a position conjugate with the focal point of the objective lens; a plurality of photodetectors for detecting the light from the specimen, passing through the confocal aperture; a dispersion element for spatially decomposing a light beam passing through the confocal aperture into a spectrum; and a wavelength selective means for receiving a part of the light beam decomposed into a spectrum to deflect it toward any of the plurality of photodetectors. In this case, it is also favorable that the amplitude distribution of the laser beam incident on the pupil of the objective lens is a nearly Gaussian distribution and a beam diameter defined as 1/e is smaller than the pupil diameter of the objective lens.

The excitation light irradiating the specimen through the objective lens is reflected and scattered by the specimen and is collected on the wavelength selective means through the same path as in the emission light. The intensity distribution of this collected spot depends on the amplitude distribution with the pupil of the objective lens, formed by excitation light which is reflected and scattered by the specimen. Since such reflected and scattered light from the specimen holds the amplitude distribution of an incident laser beam to some degree, a proper amplitude distribution is imparted to the incident laser beam, thereby providing the same function as in the case where the apodization is applied to the light beam passing through the confocal aperture. In particular, as mentioned above, the fact that the amplitude of the Gaussian distribution is imparted to the light beam brings about the effect that the side lobe of the collected spot is reduced.

However, when the beam diameter defined as 1/e is larger than the pupil diameter of the objective lens, the incident laser beam is such that the amplitude distribution is truncated with the pupil of the objective lens and is made unclear by scattering by the specimen. As a result, the amplitude distribution approaches a uniform distribution so that the effect that the side lobe of the spot is reduced is practically lost.

In accordance with the embodiments shown in the drawings, the present invention will be described below.

Figure 5:
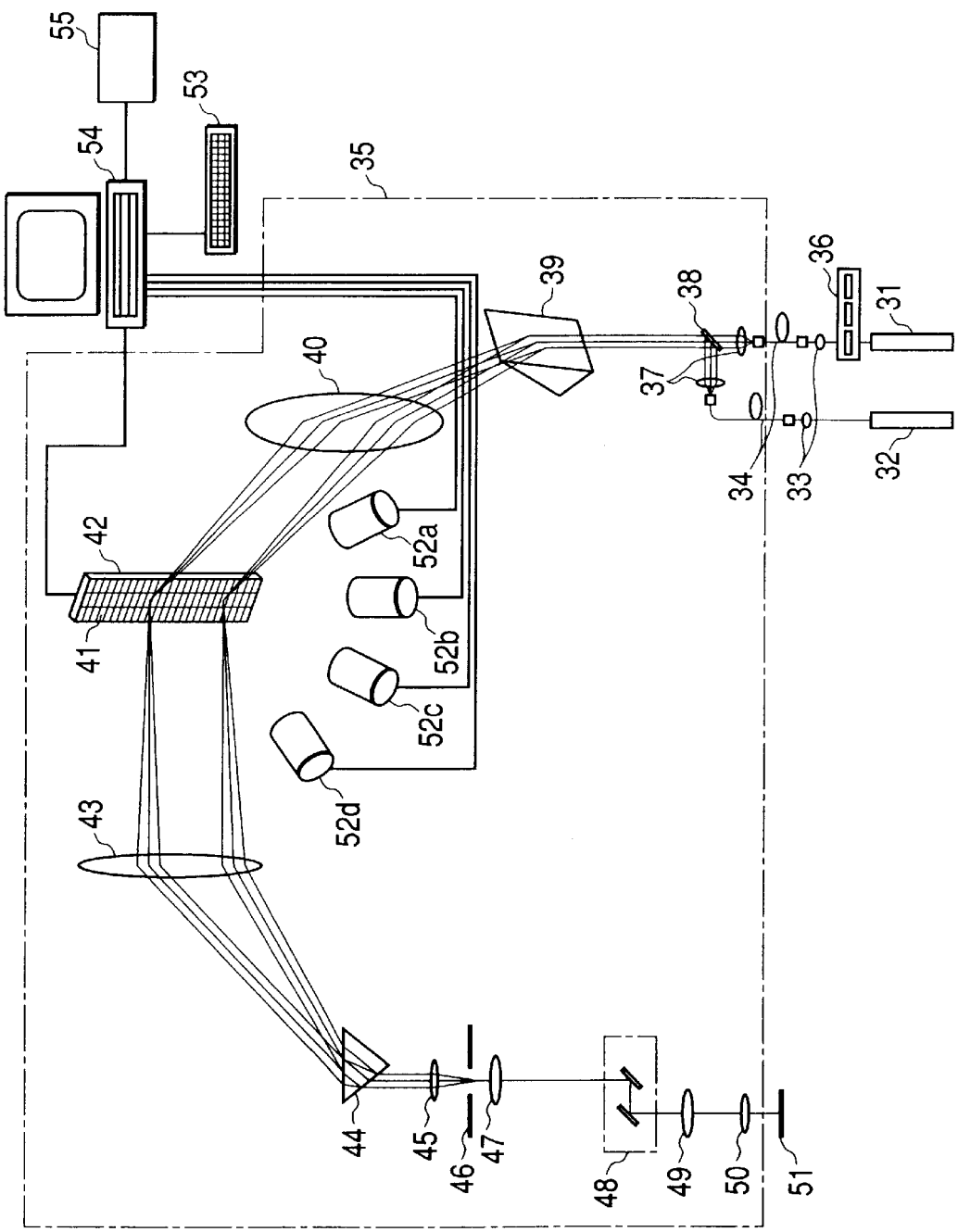
FIG. 5 is a view showing a first embodiment in the scanning optical apparatus of the present invention
Figure 6A:
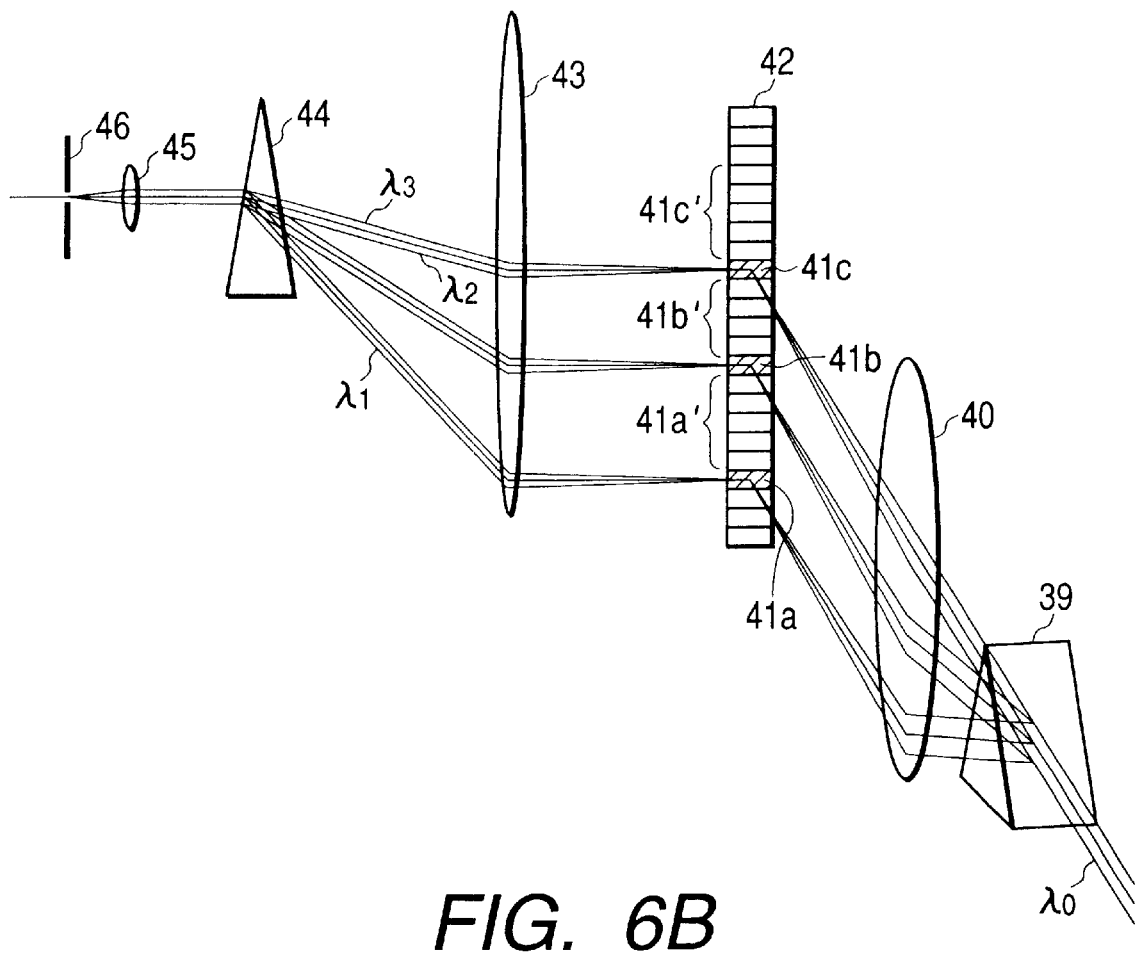
FIGS. 6A and 6B are views showing states of wavelength selections in the first embodiment.
Figure 6B:
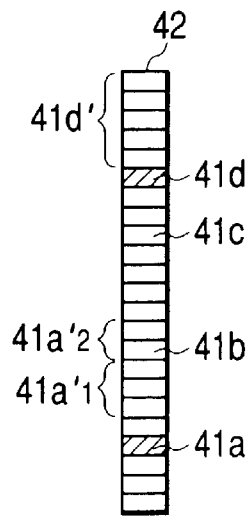
Figure 7A:
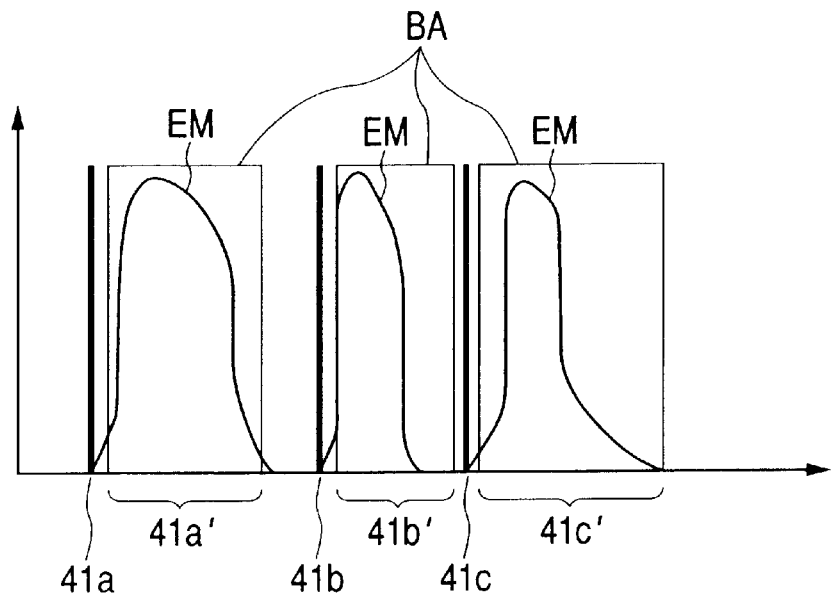
FIGS. 7A and 7B diagrams showing relationships between a mirror position and fluorescence and excitation wavelengths in the first embodiment.
Figure 7B:
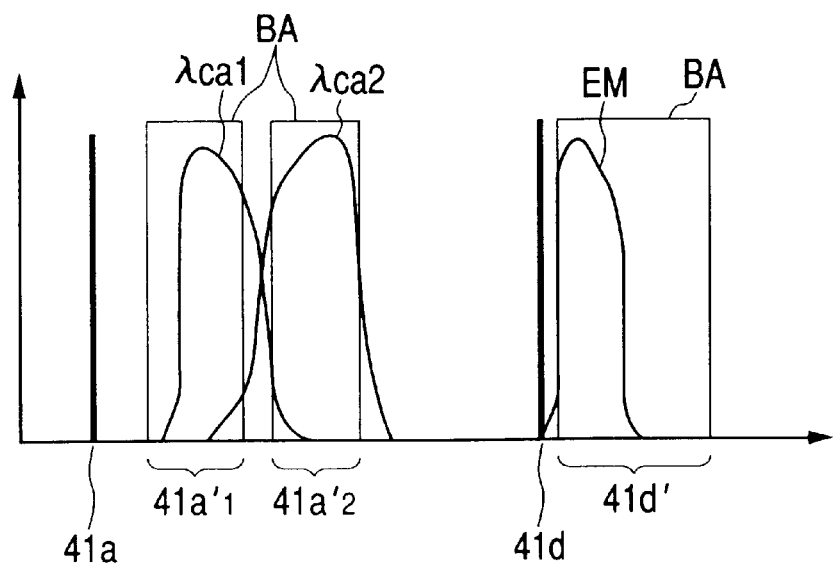

FIG. 5 shows the entire construction of the first embodiment in the scanning optical apparatus of the present invention. FIG. 6A shows positions of excitation light and emission light, incident on a mirror array and FIG. 6B shows changes of positions of the excitation light and the emission light, incident on the mirror array where the wavelength of the excitation light and the fluorescent dye are changed. FIGS. 7A and 7B show relationships between a micromirror position and excitation and fluorescence wavelengths.

The first embodiment uses a multiline Kr—Ar laser 31 oscillating wavelengths of 488 nm, 568 nm, and 647 nm simultaneously and an Ar laser 32 oscillating a wavelength of 351 nm as a light source unit. Laser beams emitted from the lasers 31 and 32 pass through single-mode fibers 34, through fiber coupling lenses 33, and are introduced into a body 35 of the scanning optical apparatus. A laser beam emitted from the laser 31 is such that its excitation wavelength is selected by a laser line filter 36. The laser beams introduced into the body 35 are converted into parallel beams with proper beam diameters by beam collimating lenses 37. The laser beams emitted from the two lasers 31 and 32 are mixed by a dichroic mirror 38.

A mixed laser beam is decomposed in accordance with the wavelength by a prism 39 which is the spectrum decomposing element and is collected through a collector lens 40 on a mirror array 42 which is the light-deflecting microelement array. Here, the mirror array 42 is such that a large number of mirror microelements 41 which are the light-deflecting microelements are arranged one- or two-dimensionally. The laser beam incident on the prism 39 is collected on corresponding one of the mirror microelements varying with the wavelength because an angle at which the laser beam is refracted by the prism differs with the wavelength. That is, the wavelength information of an incident laser beam is converted into positional information on the mirror array 42, and thereby each of the mirror microelements 41 is digitized as one unit of the wavelength information. Each of laser beams incident on the mirror microelements 41 varying with the wavelength is deflected by one of a plurality of reflection angles of the mirror microelements 41 so that the laser beams are collected at a confocal aperture 46 through a collector lens 43, a prism 44, and a collimating lens 45. The prisms 39 and 44 are equal in the amount of dispersion and are disposed at optically conjugate positions, and the collector lens 40 and 43 are selected to have the same focal length. Thus, the laser beams separated in accordance with wavelengths on the mirror array 42, after passing through the prism 44, are mixed on the same optical axis. A mixed laser beam passing through the confocal aperture 46, after being collimated by an imaging lens 47, is deflected by an X-Y scanning optical system 48 as a scanning means, such as a galvanometer mirror, and travels through a pupil relay lens 49 and an objective lens 50 so that a specimen 51 is scanned two-dimensionally with a spot. Emission light emanating from the specimen 51, excited by the irradiation of the laser beam, follows a path from the objective lens 50 to the imaging lens 47 and passes through the confocal aperture 46.

A fluorescent beam which passes through the confocal aperture 46 and is rendered parallel by the collimating lens 45 is such that its wavelength information is converted into positional information on the mirror array 42 by the prism 44 and the collector lens 43. Since, as mentioned above, the prisms 39 and 44 are equal in the amount of dispersion and the focal lengths of the collector lenses 40 and 43 are the same, a separated wavelength of the incident laser beam corresponds to that of the fluorescent beam from the specimen 51 on the mirror array 42, with a one-to-one correspondence. Here, each of the prisms 39 and 44 may be replaced with another spectrum decomposing element such as a grating, an acoustic optical element, or a holographic element. Each of collector lenses 40 and 43 may also be replaced with any optical system that has a power in the direction of spectral decomposition as in a cylindrical lens.

Each of the mirror microelements 41 has five selectable reflection angles which are deflection angles for reflecting light beams incident thereon toward photodetectors 52a, 52b, 52c, and 52d and for irradiating the specimen 51 with an excited laser beam through the confocal aperture 46. The selection of the angles can be made through an input section 53 by an electrical signal from a control section 54, with one element unit. When information on the kinds of laser light sources and fluorescent dyes used or on their combinations is inputted through the input section 53, the control section 54 fetches information relative to the angles of the mirror microelements 41 stored in a memory section 55 so that the optimum measuring condition can be always reproduced. Conversely, some angle condition of each of the mirror microelements 41 can also be stored in the memory section 55.

The dispersion of multiple emission light passing through the confocal aperture 46, separated according to wavelengths and projected on the mirror array 42, is achieved in such a way that the mirror microelements 41 corresponding to fluorescence wavelengths reflect emission light toward the different photodetectors 52a, 52b, 52c, and 52d in accordance with the kind of emission light. The intensity of the emission light is detected by each of the photodetectors. Although, in this case, laser light reflected and scattered by the specimen 51 also reaches the mirror array 42 through the confocal aperture 46, the mirror microelements 42 corresponding to wavelengths of the laser light reflect the laser light toward the direction of incidence of a laser for excitation. Hence, the laser light is not detected by any of the photodetectors 52a, 52b, 52c, and 52d.

According to the first embodiment, as mentioned above, the dispersion of light in the simultaneous detection of the multiple emission light is achieved by only single reflection, irrespective of the number of fluorescent beams to be separated and detected, and thus a loss of the amount of light is minimized. Furthermore, since a dichroic mirror for excitation, a dichroic mirror for separation, and a barrier filter which have been required in the past are not used, losses of the excitation light and the emission light are reduced and the detection of an ideal fluorescent image can be accomplished.

Subsequently, reference is made to the case where the excitation wavelength and the fluorescent dye are changed. At the beginning, a first state is described in which the specimen 51 is stained with three kinds of fluorescent dyes excited by excitation wavelengths of 351 nm, 488 nm, and 568 nm. In this case, as depicted in FIG. 6A, a laser beam $\lambda_0$ of a three-wavelength mixture on a common optical axis is separated through the prism 39 and the collector lens 40 into light beams $\lambda_1$, $\lambda_2$, and $\lambda_3$ in this order from the short-wavelength side, in accordance with wavelengths, and individual light beams are collected on mirror microelements 41a, 41b, and 41c, respectively. The mirror microelements 41a, 41b, and 41c deflect individual laser beams at angles that cause the laser beams to pass through the confocal aperture 46, through the collector lens 43, the prism 44, and the collimating lens 45. The emission light emanating from the specimen 51, after passing through the confocal aperture 46, is decomposed through the collimating lens 45, the prism 44, and the collector lens 43 into a spectrum on the mirror array 42, and fluorescent beams are projected on mirror microelements 41a', 41b', and 41c' of the mirror array 42. The fluorescent beams incident on the mirror microelements 41a', 41b', and 41c' are reflected toward the photodetectors 52a, 52b, and 52c, respectively, so that their respective amounts of light are detected. The relationship between a micromirror position and excitation and fluorescence wavelengths is shown in FIG. 7A. In FIG. 7A, the abscissas are the positions of the mirror microelements and the ordinates are the intensities of the excitation light and the emission light, reaching the mirror array 42. Reference symbol BA denotes detectable fluorescent wavelength regions and EM denotes the dispersion characteristics of the emission light.

Next, with reference to FIG. 6B, a description is given of a second state where the Kr—Ar laser is replaced by an He—Ne laser with an oscillation wavelength of 633 nm to carry out the excitation with laser beams of two wavelengths of 351 nm and 633 nm. It is assumed that the specimen 51 is stained with two kinds of fluorescent dyes, one of which is Indo-1 that changes the wavelength of emission light emitted, depending on the calcium concentration of its stained portion, by the irradiation of excitation light with a wavelength of 351 nm. This fluorescent dye generally has widespread use because fluorescence intensities are separately detected in two wavelength regions of a wavelength band 380–420 nm on the short-wavelength side and a wavelength band 470–520 nm on the long-wavelength side to obtain the ratio between these intensities, and thereby the calcium concentration can be monitored. As another fluorescent dye, Cy 5 is used and is excited by a laser beam with a wavelength of 633 nm. The second state is an example where triple emission light is detected with two-wavelength excitation as a whole.

The He—Ne laser is made to coincide in the optical axis with the Ar laser so that laser beams are incident on the prism 39 at the same angle as in the first state. The laser beams are separated in accordance with wavelengths through the prism 39 and the collector lens 40, and the laser beams with wavelengths of 351 nm and 633 nm are collected on mirror microelements 41a and 41d, respectively. The mirror microelements 41a and 41d, as in the first state, deflect the laser beams at angles that cause the laser beams to pass through the confocal aperture 46, through the collector lens 43, the prism 44, and the collimating lens 45. Thus, the emission light emanating from the specimen 51, after passing through the confocal aperture 46, is decomposed through the collimating lens 45, the prism 44, and the collector lens 43 into a spectrum on the mirror array 42. Emission light excited by the laser beam with the wavelength of 351 nm is projected at positions $41a'_1$ and $41a'_2$ of the mirror array 42, while emission light excited by the laser beam with the wavelength of 633 nm is projected at a position $41d'$ of the mirror array 42. The mirror microelements located at the positions $41a'_1$, $41a'_2$, and $41d'$ of the mirror array 42 reflect the emission light toward the photodetectors 52a, 52b, and 52c, respectively, so that the amounts of light are separately detected. In particular, the detection signals of the photodetectors 52a and 52b are transferred into information relative to the calcium concentration by calculating the ratio between them.

Care must be exercised in the case where the ratio between two fluorescence wavelengths such as that mentioned above or the ratio of a plurality of fluorescence wavelengths is required. This is because individual emission light has the intensity of light not with respect to a particular wavelength, but with respect to a certain wavelength region. When the wavelengths of two kinds of emission light approach, therefore, a region on the long-wavelength side of one emission light sometimes overlaps that on the short-wavelength side of the other. In this case, if individual emission light is measured over the entire wavelength region by the photodetectors, the intensity of emission light in a different wavelength region overlapping a desired wavelength region will also be measured, and thus a measurement error will be caused. To avoid such a measurement error, if the intensity of light is measured in a narrow wavelength region on the opposite side of two overlapping wavelength regions, the S/N ratio will be deteriorated and the measurement error will be likewise produced because the absolute value of the intensity of light becomes small.

In order to solve this problem, the first embodiment is designed so that a wavelength region (wavelength width) and a wavelength position (for example, the central wavelength of emission light) to be detected can be selected or adjusted arbitrarily and easily, and hence it is possible to measure florescent light with a high absolute intensity, keeping the influence of the overlapping wavelength regions to a minimum. Consequently, a measurement with a high degree of accuracy can be made. Even when the ambience of measurement is changed, for example, as in the case where the fluorescence wavelength is altered in accordance with a change in pH of the specimen, the wavelength region and the wavelength position to be measured can be adjusted to accommodate the change of the ambience of measurement. In the first embodiment, as mentioned above, it is possible to effectively accommodate many applications. The relationship between a micromirror position and excitation and fluorescence wavelengths in the second state is shown in FIG. 7B. The abscissas are the positions of the mirror microelements and the ordinates are the intensities of the excitation light and the emission light, reaching the mirror array 42. Reference symbol BA denotes detectable fluorescent wavelength regions, EM denotes the fluorescence wavelength of Cy 5, and λcal and λcal2 denote the fluorescence wavelengths of Indo-1 in two states where the specimen has different calcium concentrations.

As discussed above, the optimum detection for fluorescence can be always achieved with regard to various combinations of excitation wavelengths and fluorescent dyes. This is the reason that each of the mirror microelements has a plurality of reflection angles which cause a plurality of photodetectors to selectively receive light beams and a reflection angle which causes light beams emitted from the light source unit to be collected at a position optically conjugate with the confocal aperture on the mirror microelements so that one of the plurality of reflection angles can be selected at will. Thus, in the first embodiment, a multiple excitation fluorescent image of a multiply stained specimen can be obtained with a high S/N ratio, by a simple structure which does not use optical filters and dispenses with a mechanical drive requiring a high degree of accuracy of positional reproducibility, and without changing the construction of the apparatus with respect to various combinations of excitation wavelengths with fluorescent dyes.

Figure 8:
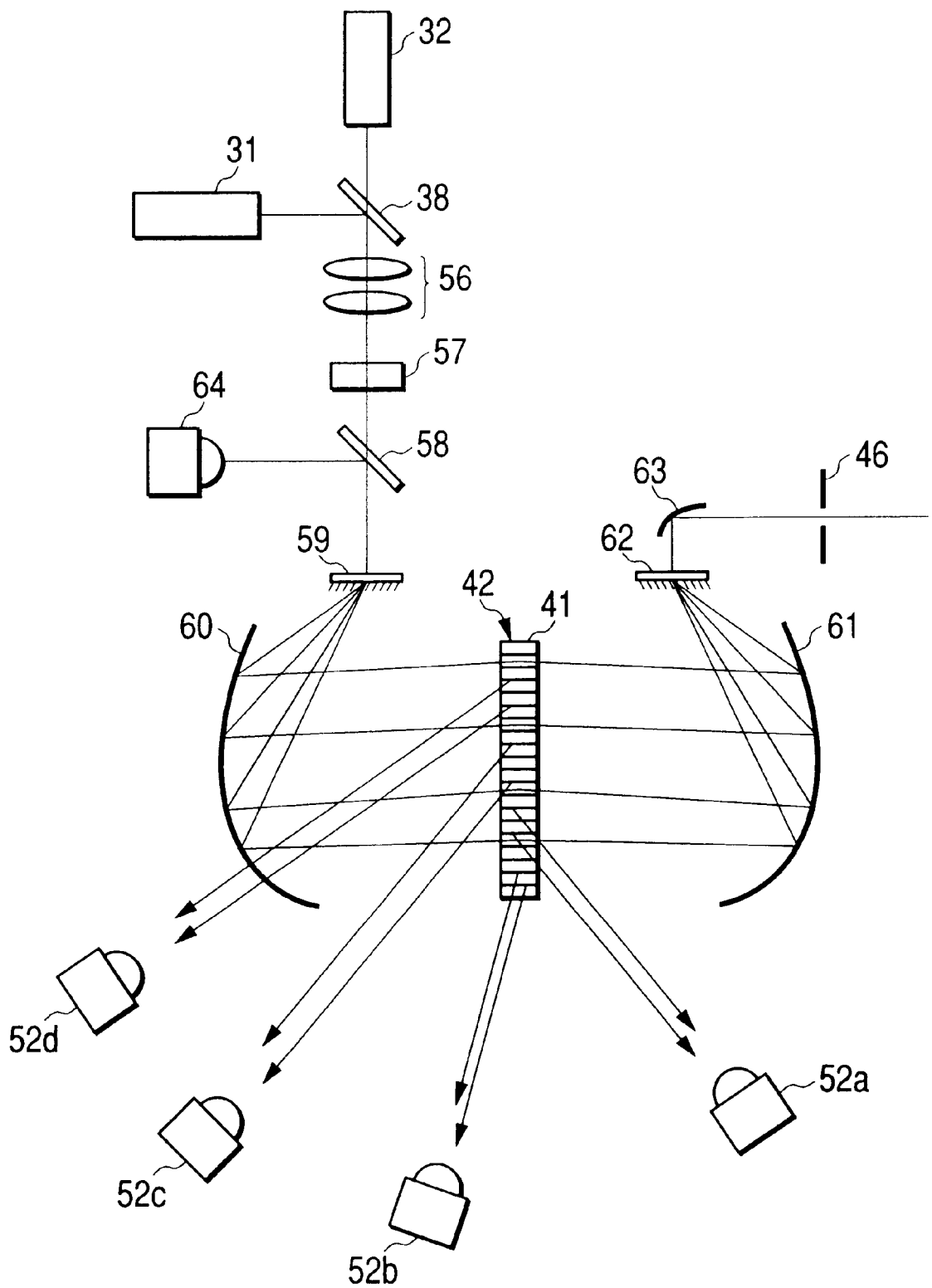
FIG. 8 is a view showing essential parts of a second embodiment in the scanning optical apparatus of the present invention.

FIG. 8 shows essential parts of the second embodiment in the scanning optical apparatus of the present invention. In this figure, an optical arrangement ranging from the specimen to the confocal aperture 46, which is the same as in the first embodiment, is omitted, and like numerals are used for like elements with respect to the first embodiment. In the second embodiment, the multiline Kr—Ar laser 31 emitting laser beams with wavelengths of 488 nm, 568 nm, and 647 nm simultaneously and the Ar laser 32 emitting a laser beam with a wavelength of 351 nm are used as a light source unit. Individual laser beams, after being mixed on the same optical axis through the dichroic mirror 38, are converted by a beam expander 56 into a parallel beam with a proper beam diameter, which is transmitted through an optical isolator 57. The optical isolator 57 serves to stabilize a laser output by blocking return light of a laser beam reflected and scattered by the specimen. The laser beam transmitted through the optical isolator 57 passes through a beam splitter 58 and is collected on the mirror array 42 after its wavelength information is transferred into the positional information of the mirror microelements 41 by a grating 59 and a collector mirror 60.

The laser beam incident on the mirror microelements 41 varying with the wavelength is deflected toward the confocal aperture 46, through a collector mirror 61, a grating 62, and a collimating mirror 63, by one of a plurality of reflection angles of the mirror microelements 41. In this process, laser beams with individual wavelengths separated in accordance with wavelengths are necessarily mixed on the same axis by the grating 62 located at a position optically conjugate with the grating 59 and having a dispersion property identical therewith and the collector mirror 61 equal in focal length to the collector mirror 60. The collector mirrors 60 and 61 and the collimating mirror 63 do not produce chromatic aberration and can be constructed to be more compact than a refraction optical system. The emission light from the specimen, excited by the laser beam passes through the confocal aperture 46 and is rendered parallel by the collimating mirror 63. By the grating 62 and the collector mirror 61, its wavelength information is converted into positional information on the mirror array 42. The detection of multiple emission light incident on the mirror array 42 is made as in the first embodiment.

However, there is the possibility that when the laser light reflected and scattered by the specimen and lens surfaces passes through the confocal aperture 46 and returns to the mirror array 42, laser light scattered by gaps between the mirror microelements 41 and their surface flaws is also detected by the photodetectors 52a, 52b, 52c, and 52d. In this case, a mixture of excitation light and emission light causes the degradation of the S/N ratio. In order to exclude the influence of such a noise of excitation light, the second embodiment is such that the return light of the laser light is split by the beam splitter 58 and monitored by a photodetector 64 and, on the basis of this detection data, the intensity of excited laser light mixed with the emission light is eliminated from the intensities of light detected by the photodetectors 52a, 52b, 52c, and 52d. Thus, a mirror is first located at the position of the specimen, and the amount of reflected light from the mirror is detected by each of the photodetectors 52a, 52b, 52c, and 52d and the photodetector 64 to previously find the ratio between the intensity of light measured by the photodetector 64 and the intensity of light detected by each of the photodetectors 52a, 52b, 52c, and 52d. Where the specimen is actually observed, it is only necessary to compensate the outputs of the photodetectors 52a, 52b, 52c, and 52d in accordance with the above ratio, on the basis of the intensity of the laser light reflected from the specimen and detected by the photodetector 64. The measurement with the mirror is basically made once, but may also be made each time the apparatus is used.

The above description is based on the assumption that the laser light reflected from the specimen is scattered by the mirror array 42. The influence of scattered light of the excited laser beam incident directly on the mirror array 42 is compensated in such a way that laser beams are emitted in the absence of the specimen and are previously measured, as background noises, by the photodetectors 52a, 52b, 52c, and 52d.

In the second embodiment constructed as stated above, a multiple excitation fluorescent image of a multiply stained specimen can be obtained with a high S/N ratio, by a simple structure which does not use optical filters and dispenses with a mechanical drive requiring a high degree of accuracy of positional reproducibility, and without changing the construction of the apparatus with respect to various combinations of excitation wavelengths with fluorescent dyes. Furthermore, the excited laser beam is detected alone, and the noise of the excitation light contained in the emission light is estimated and compensated. By doing so, even though the emission light is faint, a sharp image with little noise can be obtained.

Figure 9:
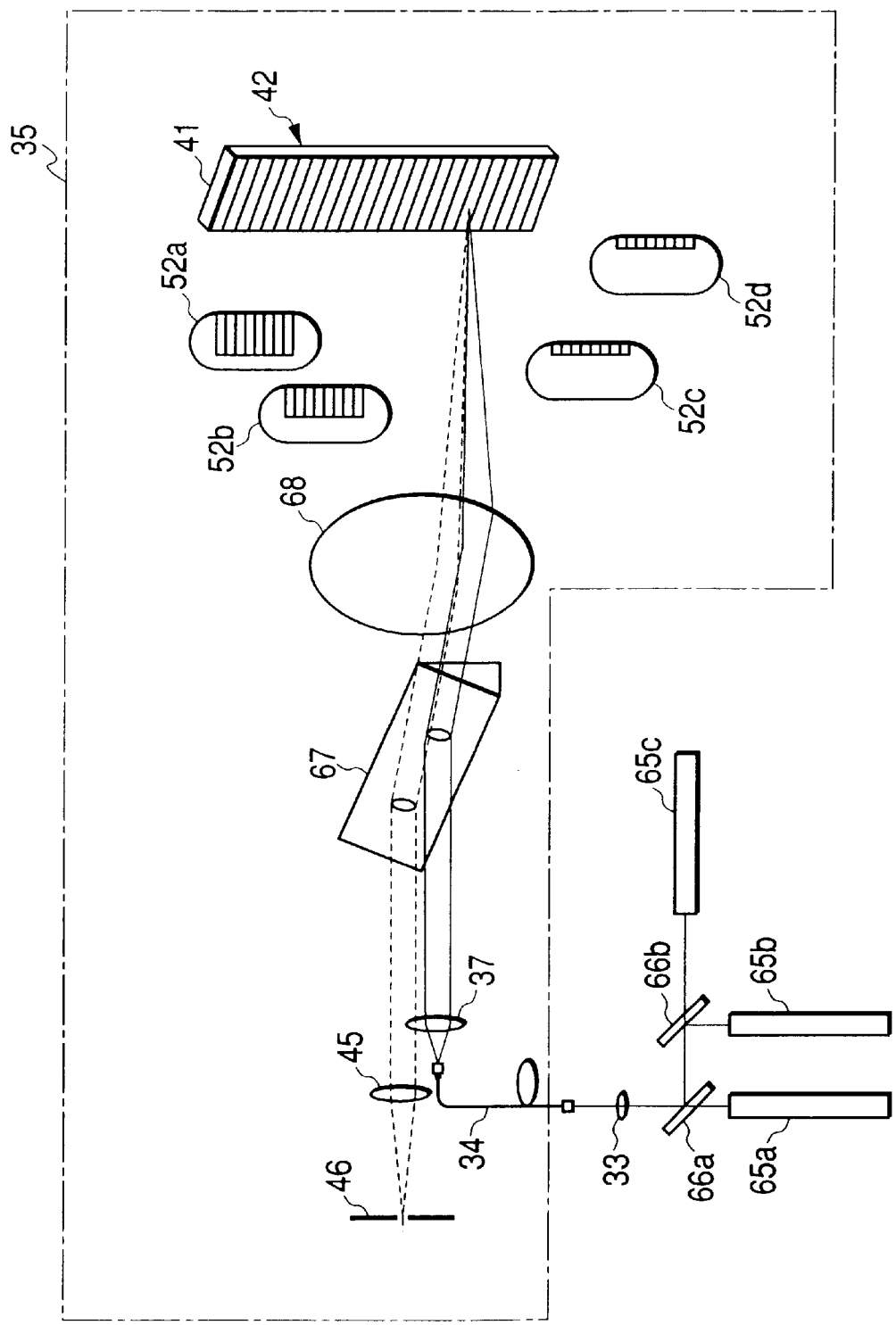
FIG. 9 is a view showing essential parts of a third embodiment in the scanning optical apparatus of the present invention.

FIG. 9 shows essential parts of the third embodiment in the scanning optical apparatus of the present invention. In this figure, an optical arrangement ranging from the specimen to the confocal aperture 46, which is the same as in the first embodiment, is omitted, and like numerals are used for like elements with respect to the first embodiment. The third embodiment uses, as a light source unit, an Ar laser 65a emitting a laser beam with a wavelength of 488 nm, an He—Ne laser 65b emitting a laser beam with a wavelength of 543 nm, and an He—Ne laser 65c emitting a laser beam with a wavelength of 633 nm. Individual laser beams are combined on a common optical axis by dichroic mirrors for combination 66a and 66b. A combined laser beam then passes through the single-mode fiber 34 through the fiber coupling lens 33 and is introduced into the body 35 of the scanning optical apparatus. The laser beam emerging from the fiber 34 is enlarged to a proper diameter by the beam collimating lens 37 and is decomposed in wavelength by a prism 67 so that a collector lens 68 causes the wavelength to correspond to the positional information of the mirror microelements 41 of the mirror array 42. Laser beams incident on the mirror microelements 41 varying with the wavelength, after being reflected by their surfaces, pass through the collector lens 68 and the prism 67 which are identical with the case of incidence, and are mixed on almost the same optical axis. A mixed laser beam leaving the prism 67 is collected by the collimating lens 45 so as to pass through the confocal aperture 46.

Each of the mirror microelements 41 is such that some reflection angles can be selected. For the mirror microelements on which laser beams are incident, angles that cause the laser beams to pass through the confocal aperture 46 are selected. The prism 67 and the collector lens 68 are arranged so that each of the laser beams is incident nearly perpendicular to the mirror array 42, irrespective of wavelength. The emission light from the specimen, excited by the laser beam passes through the confocal aperture 46 and after being rendered parallel by the collimating lens 45, travels through the prism 67 and the collector lens 68. In this way, its wavelength information is converted into positional information on the mirror array 42, and the detection of multiple emission light incident on the mirror array 42 is made as in the first embodiment.

In the third embodiment, a multiple excitation fluorescent image of a multiply stained specimen can be obtained with a high S/N ratio, by a simple structure which does not use optical filters and dispenses with a mechanical drive requiring a high degree of accuracy of positional reproducibility, and without changing the construction of the apparatus with respect to various combinations of excitation wavelengths with fluorescent dyes. Furthermore, an incident laser beam and the emission light from the specimen are separated in accordance with wavelengths by the same prism 67 and collector lens 68, and thus separated laser beams can be securely mixed on the same optical path. In addition, it is easy to make the amounts of separation of wavelengths of the incident laser beam and the emission light to coincide completely on the mirror array 42, and it is avoidable that wavelength resolution is degraded by the fabrication errors of optical parts relating to the wavelength separation. Since the excitation light and the emission light are separated in accordance with wavelengths by the same optical system, the entire apparatus can be constructed to be compact.

In any of the above embodiments, reference has been made to the case where the lasers are used as a light source unit, but the present invention is not limited to this case.

Figure 10:
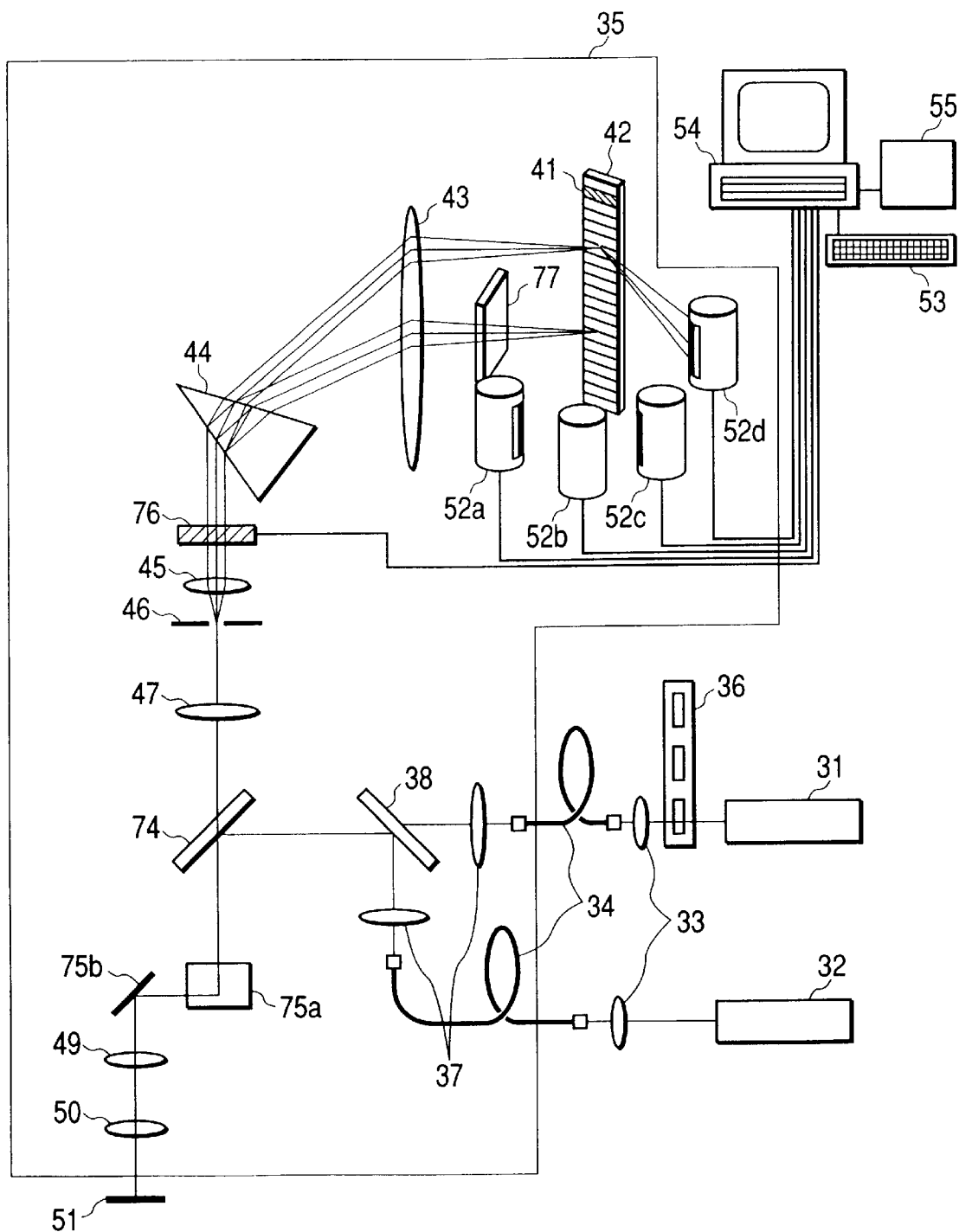
FIG. 10 is a view showing schematically the configuration of a fourth embodiment in the scanning optical apparatus of the present invention.

FIG. 10 shows a schematic configuration of the fourth embodiment in the scanning optical apparatus of the present invention. This embodiment uses the multiline Kr—Ar laser 31 oscillating three wavelengths of 488 nm, 568 nm, and 647 nm simultaneously and the Ar laser 32 oscillating a wavelength of 351 nm as a light source unit. Laser beams emitted from the lasers 31 and 32 pass through the single-mode fibers 34, through the fiber coupling lenses 33, and are introduced into the body 35 of the scanning optical apparatus. A laser beam emitted from the laser 31 is such that one of the above three wavelengths is selected as an excitation wavelength by the laser line filter 36. The laser beams introduced into the body 35 are converted into parallel beams with proper beam diameters by the beam collimating lenses 37. The laser beams emitted from the two lasers 31 and 32 are mixed by a dichroic mirror 38.

A mixed laser beam, after being reflected by a dichroic mirror for excitation 74, is deflected in a plane perpendicular to the figure by a first galvanometer mirror 75a and in a plane parallel to the figure by a second galvanometer mirror 75b. The laser beam then travels through the pupil relay lens 49 and the objective lens 50 to scan the specimen 51 as a laser spot.

The emission light from the specimen 51, excited by the irradiation of the laser beam, returns a path from the objective lens 50 to the dichroic mirror 74, and after being transmitted through the dichroic mirror 74 and collected by the collector lens 47, passes through the confocal aperture 46. The light passing through the confocal aperture 46 is changed to a parallel beam by the collimating lens 45, and its amplitude is modulated by a transmission type amplitude-modulated liquid crystal 76 in the same direction as the direction of deflection of the second galvanometer 75b. By the dispersion behavior of the prism 44, the wavelength information of the light beam is converted into angles at which light beams emerge from the prism 44, and the light beams form collected spots in accordance with wavelengths on the mirror array 42 through the collector lens 43.

In this case, the wavelength information converted into such angles of emergence is transferred into positional information on the mirror array 42 so that the positions of the mirror microelements 41 constituting the mirror array 42 correspond to individual wavelengths as they are. Also, the prism 44, as a dispersion element, may be replaced with another spectrum decomposing element such as a grating, an acoustic optical element, or a holographic element. The collector lens 43 may also be replaced with any optical system constructed with the lens that has a power in the direction of spectral decomposition as in a cylindrical lens.

Figure 11:
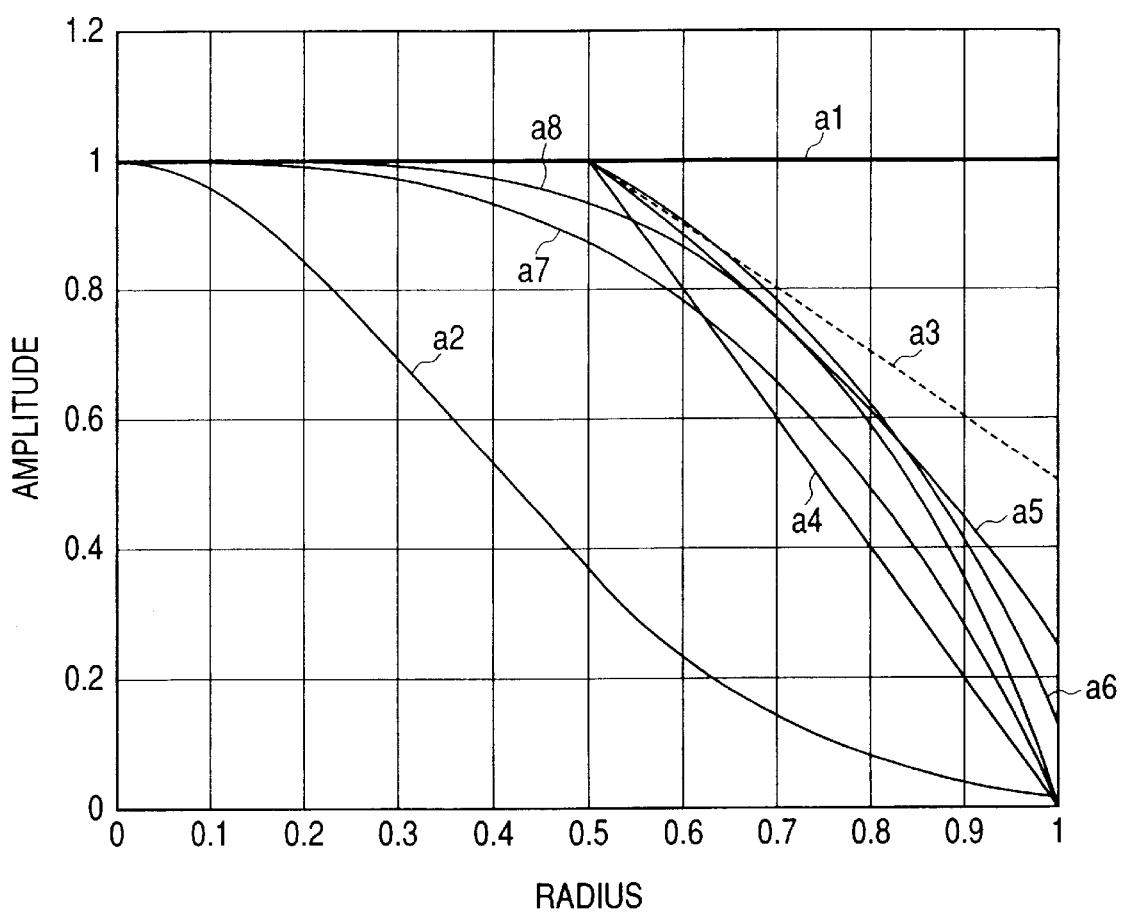
FIG. 11 is a graph showing the amplitude distribution of a light beam, imparted to a transmission type amplitude-modulated liquid crystal in the fourth embodiment.
Figure 12:
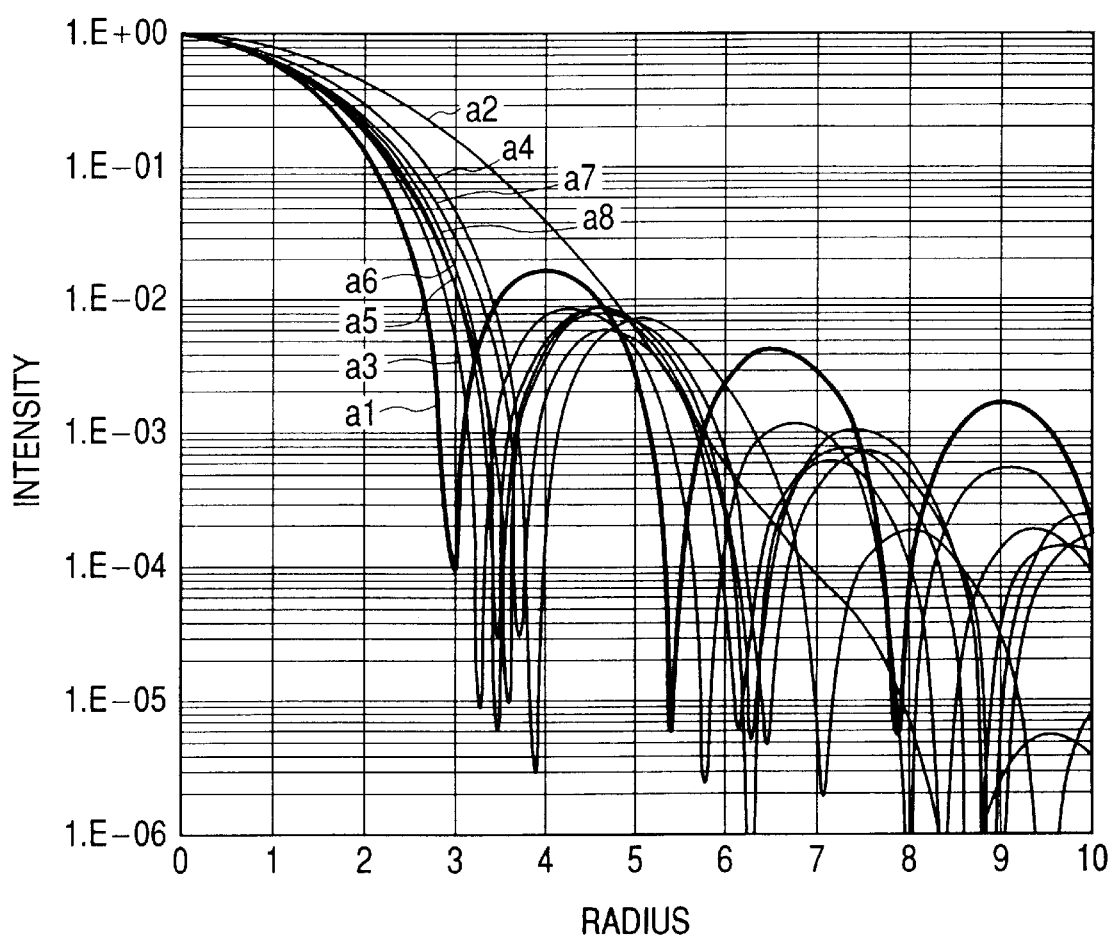
FIG. 12 is a graph showing the energy distribution of spots formed on a mirror array in the fourth embodiment.

Here, the amplitude distribution of the light beam imparted to the transmission type amplitude-modulated liquid crystal 76 is depicted in FIG. 11, with the abscissas as distances from the optical axis and the ordinates as amplitudes. The energy distribution of the spot formed on the mirror array 42 in this case is shown in FIG. 12, with the abscissas as distances from the spot center and the ordinates as intensities. Further, the distribution of energy existing outside a position spaced some distance apart from the spot center is shown in FIG. 13, with the abscissas as distances from the spot center and the ordinates as relative amounts of light where the total amount of excitation light reaching the mirror array 42 is assumed as 1.

Figure 13:
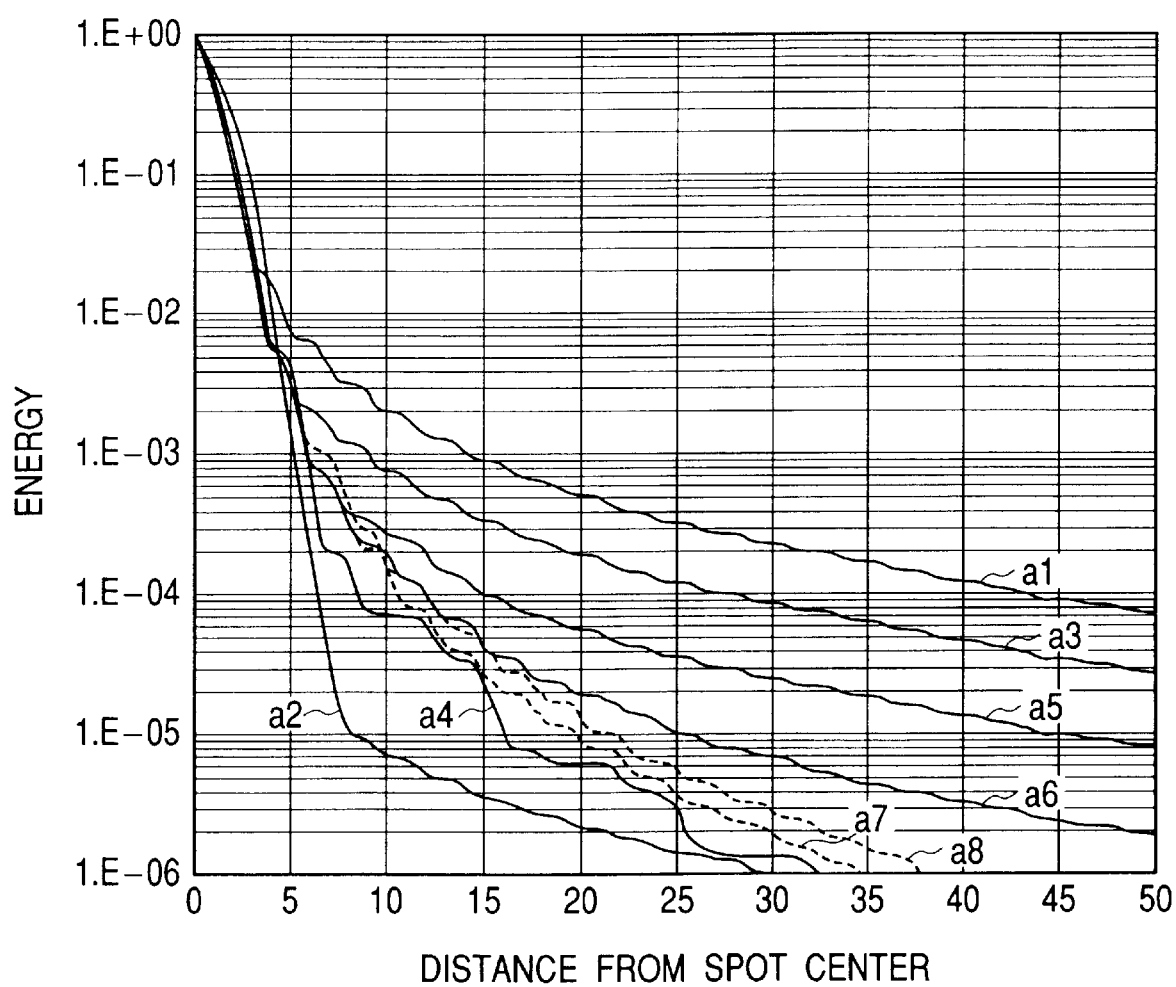
FIG. 13 is a graph showing the distribution of energy existing outside a position spaced some distance apart from the center of a in the fourth embodiment.

In FIGS. 11–13, symbols a1–a8 represent results where the apodization of the amplitude distribution defined by the following formulas is applied when a beam radius is denoted by x (the maximum is 1) and an amplitude by amp (the maximum is 1). Also, the symbol a1 is the case where the transmission type amplitude-modulated liquid crystal 76, as an apodization filter, is not placed in the optical path.

a1, amp=1 a2, $\exp(-(2x)^2)$ a3, x<0.5 amp=1, x≧0.5 amp=−x+1.5 a4, x<0.5 amp=1, x≧0.5 amp=−2x+2 a5, x<0.5 amp=1, x≧0.5 amp=$x^2$+1 a6, x<0.5 amp=1, x≧0.5 amp=−$x^3$+1 a7, amp=−$x^3$ a8, amp=−$x^4$

From FIGS. 11–13, it is seen that when the transmission type amplitude-modulated liquid crystal 76 is provided to apply the apodization, the side lobe of the spot is suppressed and thus it is possible to make the separation wavelength between excitation light and emission light close to the excitation wavelength to capture a great deal of emission light, in comparison with the case where the transmission type amplitude-modulated liquid crystal 76, as an apodization filter, is not placed in the optical path, namely the amplitude of the light beam is uniform.

When the objective lens 50 is changed, objective selective information previously stored in the memory section 55 is inputted from the input section 53 and thereby a state of the transmission type amplitude-modulated liquid crystal 76 is changed so that, from information relating to the pupil diameter and position stored in the memory section 55, the control section 54 is capable of changing the apodization region to a size suitable for the pupil diameter. When the pupil of the objective lens 50 is not located at a position conjugate with the second galvanometer mirror 75b, the transmission type amplitude-modulated liquid crystal 76 is caused to reproduce the displacement of the apodization region equivalent to the amount of movement of the light beam which corresponds to the swing angle of the galvanometer mirror previously stored so that the optical axis and the center of the apodization region can be made to always coincide.

Figures 14A, 14B, 14C, 14D, 14E, 14F:
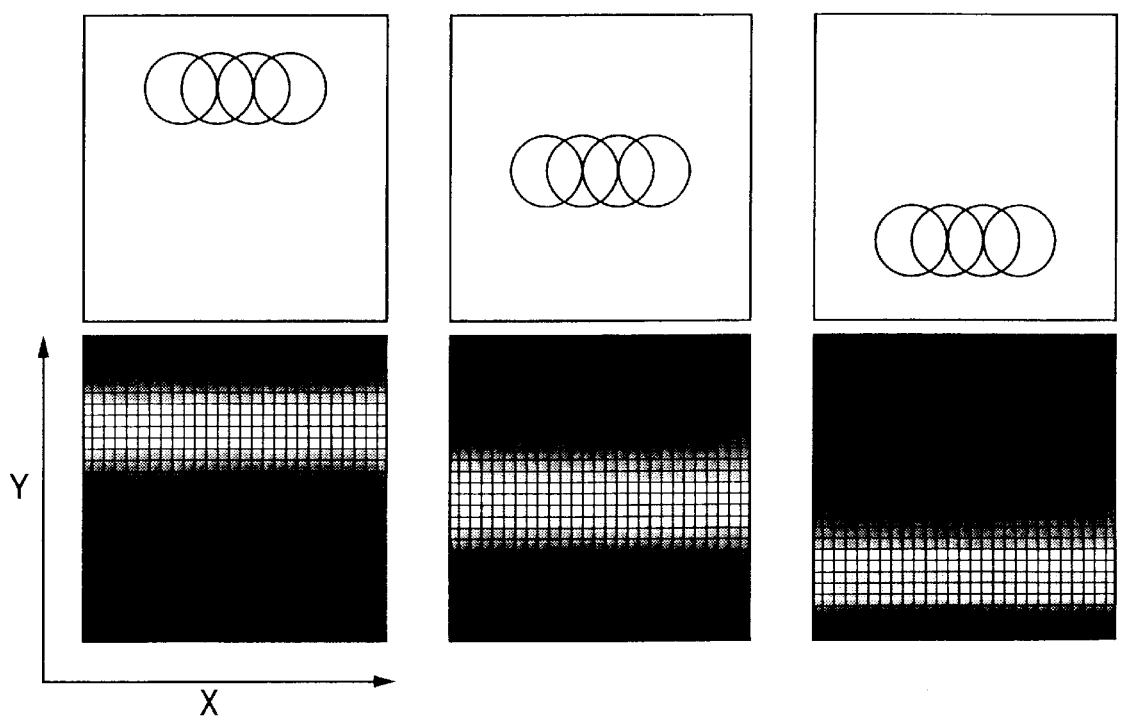
FIGS. 14A, 14B, 14C, 14D, 14E and 14F are views showing the amplitude distributions of the transmission type amplitude-modulated liquid crystal according to a change of a light beam in the fourth embodiment.

The amplitude distributions of the transmission type amplitude-modulated liquid crystal 76 in this case are illustrated in FIGS. 14A–14F. FIGS. 14A–14C show beam movements in a plane perpendicular to the optical axis at the position of the transmission type amplitude-modulated liquid crystal 76. FIGS. 14D–14F show the concentration distributions of the transmission type amplitude-modulated liquid crystal 76 associated with the beam movements in FIG. 14A–14C, respectively. The X and Y axes indicate the directions of deflections caused by the first and second galvanometer mirrors 75a and 75b, respectively, and the dispersion is performed along the Y axis. For the beam movement in the direction of the X axis, no apodization is applied, thereby preventing a decrease of the transmittance in the direction of the X axis and facilitating the control of the transmission type amplitude-modulated liquid crystal 76.

Each of the mirror microelements 41 has five selectable reflection angles which are deflection angles for reflecting light beams incident thereon toward the photodetectors 52a–52d and an angle for deflecting a light beam toward an optical trap 77. The selection of the angles can be made through an input section 53 by an electrical signal from a control section 54, with one element unit. When information relating to the lasers and the fluorescent dyes is inputted into the input section 53, the control section 54 fetches information concerning the angles of the mirror microelements 41 stored in a memory section 55 so that the optimum measuring condition can be always reproduced. Conversely, some angle condition of each of the mirror microelements 41 can also be stored in the memory section 55.

The separation of multiple emission light from the light beam is achieved in such a way that the mirror microelements corresponding to laser wavelengths reflect incident light toward the optical trap 77 and the mirror microelements corresponding to fluorescence wavelengths reflect emission light toward the different photodetectors 52a–52d in accordance with the kind of emission light. The intensity of the emission light is detected by each of the photodetectors. According to the fourth embodiment, therefore, the dispersion of light is achieved by only single reflection, irrespective of the number of multiplied fluorescent dyes, and thus a loss in the amount of light can be minimized. Moreover, changes of the excitation wavelength and the fluorescent dye can be accommodated by a proper selection of reflection angles, with each of the mirror microelements as one wavelength unit, that is, a selection of desired photodetectors.

According to the scanning optical apparatus of the fourth embodiment, as discussed above, a fluorescent image with a very high S/N ratio can be obtained by a simple structure which does not use optical filters and dispenses with a mechanical drive requiring a high degree of accuracy of positional reproducibility and with respect to various combinations of excitation wavelengths with fluorescent dyes.

Figure 15:
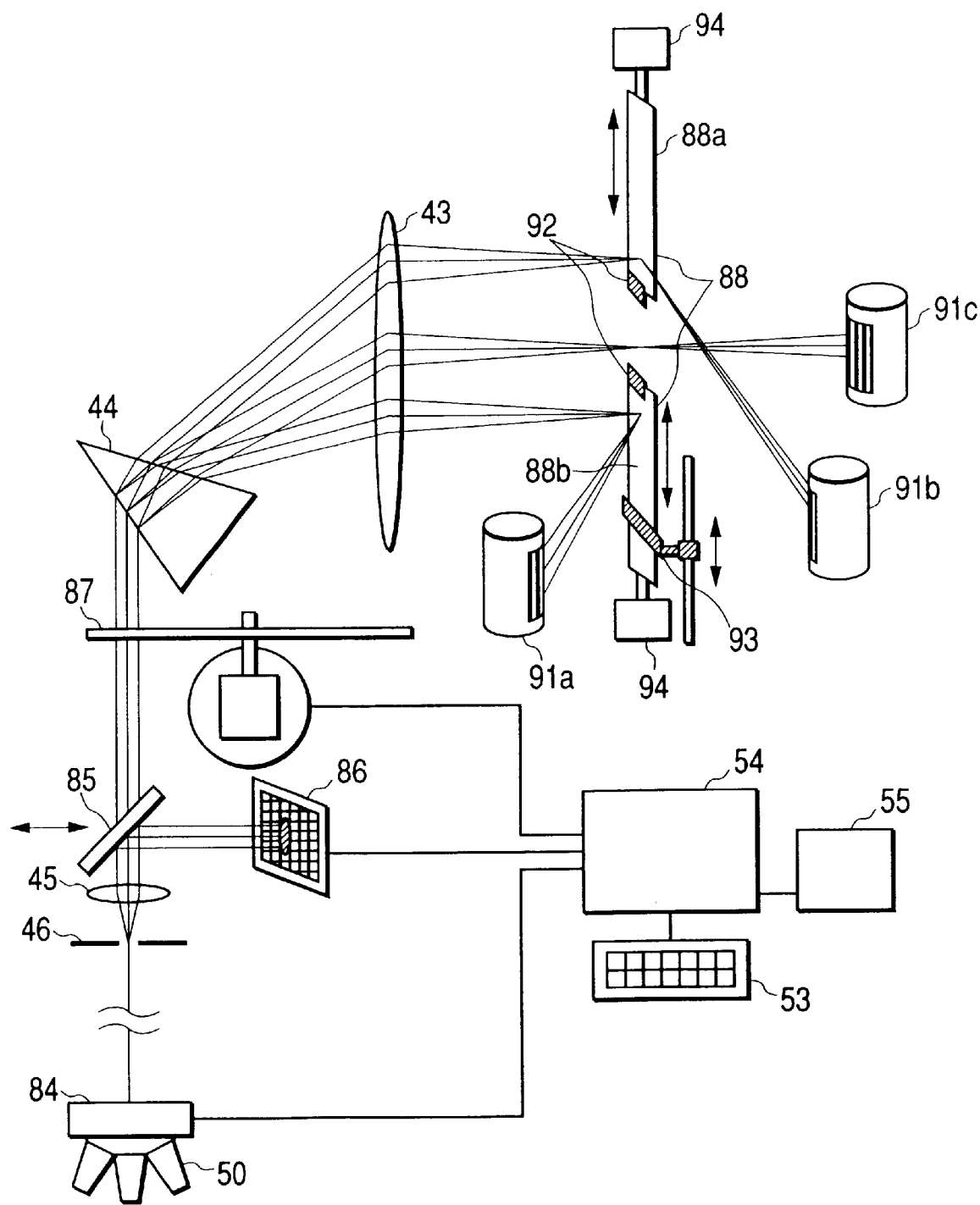
FIG. 15 is a view showing schematically the configuration of a fifth embodiment in the scanning optical apparatus of the present invention.

FIG. 15 shows a schematic configuration of the fifth embodiment in the scanning optical apparatus of the present invent. In the scanning optical apparatus of the this embodiment, an optical arrangement ranging from the laser light source unit to the confocal aperture is omitted because it is the same as in the fourth embodiment with the exception that the objective lens 50 is mounted to a rotary electrical revolver 84.

In the fifth embodiment, a divergent beam transmitted through the confocal aperture 46 is changed by the collimating lens 45 to a parallel beam, which is deflected by a mirror 85 disposed to be movable in and out of the optical path and is incident on a CCD camera 86 as an axial-displacement detector.

When the information of a selected objective lens is inputted in the input section 53 by the CCD camera 86, the rotary electrical revolver 84 is turned by a signal from the control section 54 so that a specified, selected objective lens mounted to the rotary electrical revolver 84 is placed in the optical path to scan once the specimen. In this case, the displacement of the light beam caused by a scan in using the selected objective lens is registered in the memory section 55 through the CCD camera 86. On the basis of such data, the apodization region and the amount of time displacement are determined, and an apodization filter 87 is controlled by a signal from the control section 54. Since the scanning optical apparatus is constructed so that such operation is automatically performed when the apparatus is used, the calibration of the pupil position of the objective lens relative to a manufacturing error and a device error due to an ambient change is always made with respect to the movement of the position of the light beam in the apodization region and its shape, involved in the scan, and it becomes possible to steadily detect emission light with a high S/N ratio.

Subsequently, the mirror 85 is moved outside the optical path, and the light beam changed to a parallel beam by the collimating lens 45 passes through the apodization filter 87. After its wavelength information is converted into positional information on a wavelength selective slit 88 through the prism 44 and the collector lens 43, individual light beams are collected in accordance with wavelengths.

Figure 16:
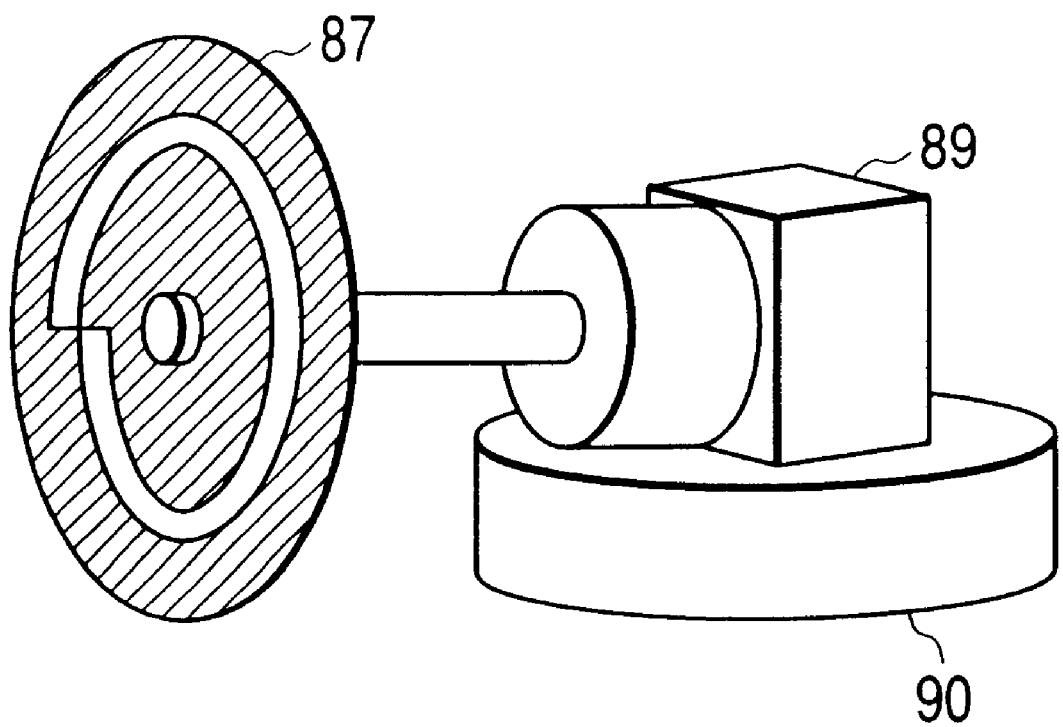
FIG. 16 is a perspective view showing an apodization filter in the fifth embodiment.

The apodization filter 87 of the fifth embodiment, as illustrated in FIG. 16, is constructed so that a portion transmitting the light beam is shaped into an annular form and the amplitude, as the apodization, is changed along the direction of its radius. The amplitude changed along the direction of the radius is such that a distance from the center of rotation is spirally changed, keeping its distribution. The apodization filter 87 is rotated by a motor 89, and thereby it is possible to shift the apodization region in the direction of the radius to follow the movement of the optical axis caused by the scan. When a movement range of the light beam varies with the kind of objective lens, it is only necessary to properly adjust the rotative speed of the motor. The apodization filter 87 and the motor 89 are both placed on a rotary stage 90, and when the apodization filter 87 is inclined with respect to the light beam, it is possible to accommodate a difference in beam diameter. The rotative speed of the motor 89 and the angle of inclination of the rotary stage 90 are controlled by the control section 54, on the basis of the result of beam detection according to the information of objective lenses stored in the memory section 55.

The light beam reaching the wavelength selective slit 88 is different in ray angle, with an optical axis of a separated wavelength as an axis, and is separated into emission light in three maximum wavelength regions, one transmission wavelength region and two reflection wavelength region, through a mirror 88a and a mirror 88b which can be moved in the direction of wavelength separation by piezoelectric elements 94. In this case, two kinds of excitation light are reflected in directions other than those of detectors 91a, 91b, and 91c through first mirrors 92 exclusively used for excitation light, provided at the edges of the mirrors 88a and 88b. The other kind of excitation light is reflected in a direction other than those of the detectors 91a–91c by a second mirror 93 exclusively used for excitation light which is movable along the mirror 88b. The emission light transmitted through or reflected by the wavelength selective slit 88 is projected on the different detectors 91a–91c so that the amount of light is detected.

As mentioned above, according to the present invention, the scanning optical apparatus can be provided in which the optimum dispersion is always achieved and a loss in the amount of emission light is materially reduced so that a multiple excitation fluorescent image can be obtained with a high S/N ratio, by a simple structure which does not use optical filters and dispenses with a mechanical drive requiring a high degree of accuracy of positional reproducibility, and without changing the construction of the apparatus with respect to various combinations of excitation wavelengths with fluorescent dyes. Further, according to the present invention, the scanning optical apparatus can be provided in which, for changes by time and ambience of the wavelength of each laser used as a light source unit, elaborate calibration work is not required and multiple emission light can be always detected with the highest S/N ratio.

Still further, according to the present invention, the scanning optical apparatus in which a loss in the amount of emission light is materially reduced and a high S/N ratio is obtained can be provided.

What is claimed is:

1. A scanning optical apparatus comprising:
   a light source unit;
   an objective lens for collecting illumination light emitted from said light source unit on a specimen;
   scanning means for relatively moving collected light and said specimen;
   an imaging optical system for imaging light emanating from said specimen;
   a confocal aperture placed at a position conjugate with a focal point of said objective lens;
   a plurality of photodetectors for detecting the light from said specimen, passing through said confocal aperture;
   a first spectrum decomposing element for spatially decomposing the light passing through said confocal aperture into a spectrum; and
   a light-deflecting microelement array comprised of a plurality of light-deflecting microelements, receiving light from said first spectrum decomposing element through a first collecting optical system to deflect the light toward said photodetectors,
   wherein said light source unit is located at a position where the illumination light is incident through said light-deflecting microelement array on said confocal aperture and each of said light-deflecting microelements has deflection angles for selectively deflecting the light passing through said confocal aperture toward said plurality of photodetectors and an deflection angle for deflecting the light from said light source unit toward said confocal aperture so that each of said light-deflecting microelements is capable of selecting one of these deflection angles.

2. A scanning optical apparatus according to claim 1, wherein a second spectrum decomposing element equal in an amount of spectrum separation to said first spectrum decomposing element and a second collecting optical system for collecting light from said second spectrum decomposing element on said light-deflecting microelement array are interposed between said light source unit and said light-deflecting microelement array.

3. A scanning optical apparatus according to claim 1, wherein a single-mode fiber is interposed between said light source unit and said second spectrum decomposing element.

4. A scanning optical apparatus according to claim 3, wherein a coupling optical system for rendering light with a plurality of wavelengths incident on said single-mode fiber is provided.

5. A scanning optical apparatus according to claim 2, wherein an optical isolator is interposed between said light source unit and said second spectrum decomposing element.

6. A scanning optical apparatus according to claim 1, wherein the following condition is satisfied:

$$0.2 < NA1/NA2 < 3$$

where NA1 is a numerical aperture of light passing through said confocal aperture, incident on said light-deflecting microelement array and NA2 is a numerical aperture of light incident from said light source unit on said light-deflecting microelement array.

7. A scanning optical apparatus according to claim 2, wherein said second spectrum decomposing element is located at a position optically conjugate with said first spectrum decomposing element.

8. A scanning optical apparatus according to claim 1, wherein a control device is provided which includes a memory section for storing individual deflection angles of said light-deflecting microelements, an information input section for inputting information of wavelengths of said light source unit and fluorescent dyes, and a control section for reproducing said individual deflection angles of said light-deflecting microelements stored from information inputted by said information input section.

9. A scanning optical apparatus according to claim 1, wherein positions of said light-deflecting microelements on which light with wavelengths of said light source unit is incident are detected so that individual deflection angles of said light-deflecting microelements are determined on the basis of detected positional information.

10. A scanning optical apparatus according to claim 1, wherein said plurality of photodetectors include photodetectors for detecting emission light produced from said specimen and photodetectors for detecting light reflected by said specimen.

11. A scanning optical apparatus according to claim 1, wherein said light-deflecting microelements are mirror microelements.

12. A scanning optical apparatus comprising:
a light source unit;
an objective lens for collecting illumination light emitted from said light source unit on a specimen;
scanning means for relatively scanning said specimen with collected illumination light;
an imaging optical system for imaging light emanating from said specimen;
a confocal aperture placed at a position conjugate with a focal point of said objective lens;
a plurality of photodetectors for detecting the light from the specimen, passing through said confocal aperture;
a dispersion element for spatially decomposing a light beam passing through said confocal aperture into a spectrum; and
wavelength selective means for receiving a part of the light beam decomposed into a spectrum to deflect said part toward any of said plurality of photodetectors,
wherein an apodization filter is interposed between said confocal aperture and said dispersion element.

13. A scanning optical apparatus comprising:
a light source unit;
an objective lens for collecting illumination light emitted from said light source unit on a specimen;
scanning means for relatively scanning said specimen with collected illumination light;
an imaging optical system for imaging light emanating from said specimen;
a confocal aperture placed at a position conjugate with a focal point of said objective lens;
a plurality of photodetectors for detecting the light from the specimen, passing through said confocal aperture;
a dispersion element for spatially decomposing a light beam passing through said confocal aperture into a spectrum; and
a light-deflecting microelement array arranged, at least, in a direction of spectral decomposition and receiving a part of the light beam decomposed into a spectrum to deflect said part toward any of said plurality of photodetectors,
wherein individual light-deflecting microelements have a plurality of deflection angles which cause light beams to be selectively received by said plurality of photodetectors, and an apodization filter is interposed between said confocal aperture and said dispersion element.

14. A scanning optical apparatus according to claim 12 or 13, wherein a collimating lens interposed between said confocal aperture and said first spectrum decomposing element, rendering a light beam passing through said confocal aperture substantially parallel and a collector lens for projecting a light beam decomposed into a spectrum by said first spectrum decomposing element on said light-deflecting microelement array are provided, together with an apodization filter for suppressing a side lobe of a spot of each wavelength formed by said collector lens, at least, with respect to a direction of spectral decomposition.

15. A scanning optical apparatus according to claim 12 or 13, wherein said scanning means includes at least one light-deflecting element located at a position conjugate with a pupil position of said objective lens, and a scanning direction with said light-deflecting element is equal to a direction of spectral decomposition.

16. A scanning optical apparatus according to claim 15, wherein said scanning means includes two adjacent scanning mirrors and one of said scanning mirrors is located at a position conjugate with the pupil position of said objective lens.

17. A scanning optical apparatus according to claim 12 or 13, wherein an apodization region is changed in a plane perpendicular to an optical axis in association with said scanning means.

18. A scanning optical apparatus according to claim 12 or 13, wherein an apodization filter includes a spatial optical modulator in which amplitude modulation is possible.

19. A scanning optical apparatus according to claim 12 or 13, wherein an apodization filter is constructed so that an amplitude of a light beam is modulated only in a direction of spectral decomposition.

20. A scanning optical apparatus according to claim 12 or 13, wherein an input section for inputting information of objective lenses, a memory section for storing an amplitude profile of an apodization filter and a displacement of an optical axis involved in a scan, and a control section for controlling a change of an apodization region, on the basis of said input information, in association with said scanning means are provided.

21. A scanning optical apparatus according to claim 18, wherein an axial-displacement detecting means for detecting a displacement of an optical axis involved in a scan is interposed between said scanning means and said first spectrum decomposing element so that an apodization region is changed in association with said scanning means, on the basis of information secured by said detecting means.

22. A scanning optical apparatus comprising:

a light source unit;

an objective lens for collecting illumination light emitted from said laser light source unit on a specimen;

scanning means for relatively scanning said specimen with collected illumination light;

an imaging optical system for imaging light emanating from said specimen;

a confocal aperture placed at a position conjugate with a focal point of said objective lens;

a plurality of photodetectors for detecting the light from said specimen, passing through said confocal aperture;

a dispersion element for spatially decomposing a light beam passing through said confocal aperture into a spectrum; and wavelength selective means for receiving a part of the light beam decomposed into a spectrum to deflect said part toward any of said plurality of photodetectors, wherein an amplitude distribution of illumination light incident on a pupil of said objective lens is a substantial Gaussian distribution and a beam diameter defined as 1/e is smaller than a pupil diameter of said objective lens.

\* \* \* \* \*